(12) United States Patent
Sudhakar

(10) Patent No.: US 11,999,750 B2
(45) Date of Patent: Jun. 4, 2024

(54) CRYSTALLINE FORMS OF (S)-5-BENZYL-N-(5-METHYL-4-OXO-2,3,4,5-TETRAHYDROPYRIDO [3,2-B][1,4]OXAZEPIN-3-YL)-4H-1,2,4-TRIAZOLE-3-CARBOXAMIDE

(71) Applicant: Denali Therapeutics Inc., South San Francisco, CA (US)

(72) Inventor: Anantha Sudhakar, South San Francisco, CA (US)

(73) Assignee: DENALI THERAPEUTICS INC., South San Francisco, CA (US)

( * ) Notice: Subject to any disclaimer, the term of this patent is extended or adjusted under 35 U.S.C. 154(b) by 0 days.

(21) Appl. No.: 18/095,621

(22) Filed: Jan. 11, 2023

(65) Prior Publication Data

US 2023/0271978 A1 Aug. 31, 2023

Related U.S. Application Data

(60) Provisional application No. 63/386,113, filed on Dec. 5, 2022, provisional application No. 63/298,816, filed on Jan. 12, 2022.

(51) Int. Cl.
*C07D 498/04* (2006.01)
*A61K 31/553* (2006.01)
*A61P 29/00* (2006.01)

(52) U.S. Cl.
CPC ........ *C07D 498/04* (2013.01); *C07B 2200/13* (2013.01)

(58) Field of Classification Search
CPC ............ C07D 498/04; C07B 2200/13; A61K 31/553; A61P 29/00
See application file for complete search history.

(56) References Cited

U.S. PATENT DOCUMENTS

| | | | |
|---|---|---|---|
| 4,477,464 A | 10/1984 | Slade et al. |
| 4,871,842 A | 10/1989 | Sugihara et al. |
| 5,055,464 A | 10/1991 | Murakami et al. |
| 5,206,234 A | 4/1993 | Bock et al. |
| 5,206,235 A | 4/1993 | Fisher et al. |
| 5,283,241 A | 2/1994 | Bochis et al. |
| 5,284,841 A | 2/1994 | Chu et al. |
| 5,310,737 A | 5/1994 | Fisher et al. |
| 5,330,987 A | 7/1994 | Allen et al. |
| 5,420,271 A | 5/1995 | Warshawsky et al. |
| 5,428,158 A | 6/1995 | Warshawsky et al. |
| 5,457,196 A | 10/1995 | Warshawsky et al. |
| 5,484,917 A | 1/1996 | Lowe, III |
| 5,596,000 A | 1/1997 | Esser et al. |
| 5,606,054 A | 2/1997 | Fisher et al. |
| 5,672,596 A | 9/1997 | Wyvratt et al. |
| 5,710,153 A | 1/1998 | Ohmoto et al. |
| 5,712,273 A | 1/1998 | Schnorrenberg et al. |
| 5,726,307 A | 3/1998 | Schoen et al. |
| 5,747,235 A | 5/1998 | Farid et al. |
| 5,783,573 A | 7/1998 | Rozsa et al. |
| 5,789,587 A | 8/1998 | Fisher et al. |
| 5,958,924 A | 9/1999 | McCort et al. |
| 6,028,195 A | 2/2000 | Cho et al. |
| 6,211,174 B1 | 4/2001 | Devita et al. |
| 6,335,363 B1 | 1/2002 | Gerlach et al. |
| 6,350,741 B1 | 2/2002 | Golec et al. |
| 6,376,484 B1 | 4/2002 | Ohmoto et al. |
| 7,098,235 B2 | 8/2006 | Sher et al. |
| 7,109,357 B2 | 9/2006 | Wannamaker et al. |
| 7,208,600 B2 | 4/2007 | Cottrell et al. |
| 7,491,743 B2 | 2/2009 | Cuny et al. |
| 7,842,686 B2 | 11/2010 | Anderson et al. |
| 7,884,074 B2 | 2/2011 | Petzelbauer et al. |
| 8,088,890 B2 | 1/2012 | Petzelbauer et al. |
| 8,242,150 B2 | 8/2012 | Fischer et al. |
| 8,569,286 B2 | 10/2013 | Hipskind et al. |
| 8,586,732 B2 | 11/2013 | Corkey et al. |
| 9,062,002 B2 | 6/2015 | Takhi et al. |
| 9,062,075 B2 | 6/2015 | Takhi et al. |
| 2003/0191049 A1 | 10/2003 | Amblard et al. |
| 2004/0002495 A1 | 1/2004 | Sher et al. |
| 2004/0142938 A1 | 7/2004 | Sher et al. |
| 2007/0010428 A1 | 1/2007 | McMurray et al. |
| 2011/0046195 A1 | 2/2011 | Blackwell et al. |
| 2011/0135600 A1 | 6/2011 | Stieber et al. |
| 2011/0152253 A1 | 6/2011 | Motoki et al. |
| 2011/0230414 A1 | 9/2011 | Hendricks et al. |
| 2011/0306626 A1 | 12/2011 | Selnick et al. |
| 2012/0315247 A1 | 12/2012 | Xi |
| 2013/0165446 A1 | 6/2013 | Fujita et al. |
| 2015/0315210 A1 | 11/2015 | Hu et al. |
| 2015/0353533 A1 | 12/2015 | Bandyopadhyay et al. |
| 2015/0374662 A1 | 12/2015 | Bode et al. |

(Continued)

FOREIGN PATENT DOCUMENTS

CL 2018002094 A1 12/2018
CL 2018002101 A1 12/2018

(Continued)

OTHER PUBLICATIONS

Bacqué et al., "Tin-free radical cyclizations for the synthesis of 7-azaoxindoles, 7-azaindolines, tetrahydro[1,8] naphthyridines, and tetrahydro-5H-pyrido[2,3-b]azepin-8-ones", Org Lett. 2004, 6(21), 3671-3674.

Berger et al., "Characterization of GSK'963: a structurally distinct, potent and selective inhibitor of RIP1 kinase", Cell Death Discovery, 2015, 1, 15009. (7 pages).

Berger et al., "Drilling into RIP1 biology: what compounds are in your toolkit?", Cell Death and Disease, 2015, 6:E1889, 2 pages.

Bolin et al., "Peptide and Peptide Mimetic Inhibitors of Antigen Presentation by HLA-DR Class II MHC Molecules, Design, Structure-Activity Relationships, and X-ray Crystal Structures", J. Med. Chem., 2000, 43, 2135-2148.

(Continued)

*Primary Examiner* — Brenda L Coleman
(74) *Attorney, Agent, or Firm* — McNeill Baur PLLC

(57) ABSTRACT

Described herein are crystalline forms of (S)-5-benzyl-N-(5-methyl-4-oxo-2,3,4,5-tetrahydropyrido [3,2-b][1,4]oxazepin-3-yl)-4H-1,2,4-triazole-3-carboxamide, the process of preparing the forms, and pharmaceutical compositions methods of use thereof.

18 Claims, 18 Drawing Sheets

(56) References Cited

U.S. PATENT DOCUMENTS

| | | | |
|---|---|---|---|
| 2017/0008878 A1 | 1/2017 | Bandyopadhyay et al. |
| 2019/0031666 A1 | 1/2019 | Ding et al. |
| 2020/0239484 A1 | 7/2020 | Ding et al. |

FOREIGN PATENT DOCUMENTS

| | | |
|---|---|---|
| CN | 103664904 | 3/2014 |
| CN | 105121432 A | 12/2015 |
| EP | 0322779 | 7/1989 |
| EP | 0462800 | 12/1991 |
| EP | 0703222 | 3/1996 |
| EP | 0728746 | 8/1996 |
| EP | 1939187 | 7/2008 |
| EP | 2493888 | 4/2016 |
| EP | 3017825 | 5/2016 |
| ES | 2081747 | 3/1996 |
| GB | 2272439 | 5/1994 |
| JP | H0334977 | 2/1991 |
| JP | H05239065 | 9/1993 |
| JP | H09295996 | 11/1997 |
| JP | 10251295 | 9/1998 |
| JP | 256318 | 9/2000 |
| JP | 035933 | 2/2005 |
| JP | 6974331 B2 | 12/2021 |
| NO | 2001074783 | 10/2001 |
| WO | 1992016524 | 10/1992 |
| WO | 1994001421 | 1/1994 |
| WO | 1994004531 | 3/1994 |
| WO | 199408683 | 4/1994 |
| WO | 1994007483 | 4/1994 |
| WO | 1994007486 | 4/1994 |
| WO | 1994024149 | 10/1994 |
| WO | 1995003290 | 2/1995 |
| WO | 1995016692 | 6/1995 |
| WO | 1995028419 | 10/1995 |
| WO | 1995030687 | 11/1995 |
| WO | 1996005195 | 2/1996 |
| WO | 1996011691 | 4/1996 |
| WO | 1996011701 | 4/1996 |
| WO | 1996011940 | 4/1996 |
| WO | 1996016008 | 5/1996 |
| WO | 1996040653 | 12/1996 |
| WO | 1996040654 | 12/1996 |
| WO | 1996040655 | 12/1996 |
| WO | 1996040656 | 12/1996 |
| WO | 1997022619 | 6/1997 |
| WO | 1998000402 | 1/1998 |
| WO | 1999007731 | 2/1999 |
| WO | 2000005246 | 2/2000 |
| WO | 2001074784 | 10/2001 |
| WO | 2001079261 | 10/2001 |
| WO | 2001090084 | 11/2001 |
| WO | 2001092235 | 12/2001 |
| WO | 2002018382 | 3/2002 |
| WO | 2002020500 | 3/2002 |
| WO | 2003007945 | 1/2003 |
| WO | 2003010141 | 2/2003 |
| WO | 2003014377 | 2/2003 |
| WO | 2003031376 | 4/2003 |
| WO | 2004002960 | 1/2004 |
| WO | 2004055008 | 7/2004 |
| WO | 2004082602 | 9/2004 |
| WO | 2004098589 | 11/2004 |
| WO | 2005056577 | 6/2005 |
| WO | 2006031606 | 3/2006 |
| WO | 2006044449 | 4/2006 |
| WO | 2006044504 | 4/2006 |
| WO | 2006059164 | 6/2006 |
| WO | 2006063178 | 6/2006 |
| WO | 2006071775 | 7/2006 |
| WO | 2006079077 | 7/2006 |
| WO | 2006103559 | 10/2006 |
| WO | 2006105222 | 10/2006 |
| WO | 2006113432 | 10/2006 |
| WO | 2006116713 | 11/2006 |
| WO | 2007035935 | 3/2007 |
| WO | 2007067416 | 6/2007 |
| WO | 2007075772 A2 | 7/2007 |
| WO | 2007109251 | 9/2007 |
| WO | 2007126871 | 11/2007 |
| WO | 2007145922 | 12/2007 |
| WO | 2008009122 | 1/2008 |
| WO | 2008040778 | 4/2008 |
| WO | 2008045484 | 4/2008 |
| WO | 2008080056 | 7/2008 |
| WO | 2008106077 | 9/2008 |
| WO | 2008135525 | 11/2008 |
| WO | 2008156580 | 12/2008 |
| WO | 2009019115 | 2/2009 |
| WO | 2009085256 | 7/2009 |
| WO | 2009095759 | 8/2009 |
| WO | 2009095788 | 8/2009 |
| WO | 2009095789 | 8/2009 |
| WO | 2009103432 | 8/2009 |
| WO | 2009105348 | 8/2009 |
| WO | 2009140549 | 11/2009 |
| WO | 2010019899 | 2/2010 |
| WO | 2010083725 | 7/2010 |
| WO | 2011035019 | 3/2011 |
| WO | 2011133964 | 10/2011 |
| WO | 2011149963 | 12/2011 |
| WO | 2012061408 | 5/2012 |
| WO | 2013000994 | 1/2013 |
| WO | 2013012918 | 1/2013 |
| WO | 2013013826 | 1/2013 |
| WO | 2013059791 | 4/2013 |
| WO | 2013151739 | 10/2013 |
| WO | 2013189241 | 12/2013 |
| WO | 2014009495 | 1/2014 |
| WO | 2014023708 | 2/2014 |
| WO | 2014072930 | 5/2014 |
| WO | 2014125444 | 8/2014 |
| WO | 2014144547 | 9/2014 |
| WO | 2014155016 | 10/2014 |
| WO | 2014170892 | 10/2014 |
| WO | 2015027137 | 2/2015 |
| WO | 2015103583 | 7/2015 |
| WO | 2015104677 | 7/2015 |
| WO | 2015184257 | 12/2015 |
| WO | 2016023918 | 2/2016 |
| WO | 2016027253 | 2/2016 |
| WO | 2016055028 | 4/2016 |
| WO | 2016101885 | 6/2016 |
| WO | 2016101887 | 6/2016 |
| WO | 2016113668 | 7/2016 |
| WO | 2016128936 | 8/2016 |
| WO | 2016168014 | 10/2016 |
| WO | 2017004500 | 1/2017 |
| WO | 2017022962 | 2/2017 |
| WO | 2017069279 | 4/2017 |
| WO | 2017109724 | 6/2017 |
| WO | 2017136727 A2 | 8/2017 |
| WO | 2021203011 A1 | 10/2021 |

OTHER PUBLICATIONS

CAS RN 1222532-89-9 Registry, 1-Piperidinecarboxamide, 4-(1,4-dihydro-2-oxo-3(2H)-quinazolinyl)-N-[2,3,4,5-tetrahydro-1-1(1methylethyl)-2-oxo-1H-1-benzazepin-3-yl]-(CA Index Name), Entered STN: May 12, 2010, Database: ChEBI (European Bioinformatics Institute) (1 page).

Cristau et al., "Reaction of lithium diphenylphosphonium di(methylide) with carbonic acid derivatives. A novel access to polyfunctional unsaturated esters and amides", Heteroatom Chemistry, 1992, 3(4), 415-422.

Degterev et al., "Identification of RIP1 kinase as a specific cellular target of necrostatins." Nature Chemical Biology, 2008, 4, 313-321.

Dhanik et al., "Binding Modes of Peptidomimetics Designed to Inhibit STAT3", PLoS ONE 7(12): e51603 (2012). (18 pages).

Fischer et al., "Discovery of novel triazolobenzazepinones as ?-secretase modulators with central Aß42 lowering in rodents and rhesus monkeys." Bioorganic & Medicinal Chemistry Letters, 2015, 25(17), 3488-3494.

(56) References Cited

OTHER PUBLICATIONS

Florence, Alastair J., "Polymorph screening in pharmaceutical development—European Pharmaceutical Review", 10 pages (Aug. 19, 2010) (retrieved from the Internet: https://www.europeanpharmaceuticalreview.com/article/3659/polymorph-screening-in-pharmaceutical-development/).
GlaxoSmithKline, "A Safety and Tolerability Study of GSK2982772, in Single (in Both Fed and Fasted States) and Repeat Oral Doses in Healthy Male Subjects." ClinicalTrials.gov, record processed Aug. 2, 2016. (14 pages).
GlaxoSmithKline, "Safety, Tolerability, Pharmacokinetics, Pharmacodynamics, and Efficacy of Repeat Doses of GSK2982772." ClinicalTrials.gov, record processed Aug. 2, 2016. (14 pages).
Harris et al., "Discovery of a First-in-Class Receptor Interacting Protein 1 (RIP1) Kinase Specific Clinical Candidate (GSK2982772) for the Treatment of Inflammatory Diseases." J Med Chem., 2017, 60(4), pp. 1247-1261.
Tarris et al., "DNA-Encoded Library Screening Identifies Benzo[b][1,4]oxazepin-4-ones as Highly Potent and Monoselective Receptor Interacting Protein 1 Kinase Inhibitors." J. Med. Chem., 2016, 59(5), pp. 2163-2178.
Herpin et al., "Directed sorting approach for the synthesis of large combinatorial libraries of discrete compounds", Methods Enzymol., 2003, 369, pp. 75-99.
Hoyt et al., "Benzazepinone Nav1.7 blockers: potential treatments for neuropathic pain." Bioorganic & Medicinal Chemistry Letters, 2007, 17(22), pp. 6172-6177.
Klapars et al., "Synthesis of medium ring nitrogen heterocycles via a tandem copper-catalyzed C—N bond formation-ring-expansion process." J Am Chem Soc., 2004, 126(11), pp. 3529-3533.
Lee, Eun Hee, "A practical guide to pharmaceutical polymorph screening & selection", Asian Journal of Pharmaceutical Sciences, 9(4), pp. 163-175 (Mar. 16, 2014).
Mandal et al., "Conformationally Constrained Peptidomimetic Inhibitors of Signal Transducer and Activator of Transcription 3: Evaluation and Molecular Modeling." J. Med. Chem., 2009, 52(8), pp. 2429-2442.
Morissette et al., "High-throughput crystallization: polymorphs, salts, co-crystals and solvates of pharmaceutical solids", Advanced Drug Delivery Reviews, 56(3), pp. 275-300 (Jan. 1, 2004).

Notification of Transmittal of The International Search Report and The Written Opinion of the International Searching Authority, or the Declaration, The International Search Report and Written Opinion mailed in corresponding International Application No. PCT/US2023/010551, dated Apr. 17, 2023 (10 pages).
Ofengeim et al., "Activation of necroptosis in multiple sclerosis." Cell Rep., 2015, 10(11), pp. 1836-1849.
Paone et al., "Orally bioavailable imidazoazepanes as calcitonin gene-related peptide (CGRP) receptor antagonists: Discovery of MK-2918," Bioorganic & Medicinal Chemistry Letters, 2011, 21, pp. 2683-2686.
Rosauer et al., "Novel 3,4-Dihydroquinolin-2(1H)-one inhibitors of human glycogen phosphorylase a." Bioorganic & Medicinal Chemistry Letters, 2003, 13(24), pp. 4385-4388.
Rosloniec et al., "Second-generation peptidomimetic inhibitors of antigen presentation effectively treat autoimmune diseases in HLA-DR-transgenic mouse models." J Autoimmun., 2006, 27(3), pp. 182-195.
Sarabu et al., "Oxazole- and Imidazole-Based Ser-Leu Dipeptide Mimetics in Potent Inhibitors of Antigen Presentation by MHC Class II DR Molecules." Drug Design and Discovery, 2002, 18(1), pp. 3-7.
Teng et al., "Structure activity relationship and liver microsome stability studies of pyrrole necroptosis inhibitors." Bioorg Med Chem Lett., 2008, 18(11), pp. 3219-3223.
Teng et al., "Structure-activity relationship study of [1,2,3]thiadiazole necroptosis inhibitors." Bioorganic & Medicinal Chemistry Letters, 2007, 17(24), pp. 6836-6840.
Teng et al., "Structure-activity relationship study of novel necroptosis inhibitors." Bioorganic & Medicinal Chemistry Letters 2005, 15, pp. 5039-5044.
Wei et al., "Modeling Ligand-Receptor Interaction for Some MHC Class II HLA-DR4 Peptide Mimetic Inhibitors Using Several Molecular Docking and 3D QSAR Techniques." J. Chem. Inf. Model., 2005, 45(5), pp. 1343-1351.
Williams et al., "Characterization of a New Class of Potent Inhibitors of the Voltage-Gated Sodium Channel Nav1.7." Biochemistry, 2007, 46(50), pp. 14693-14703.
Xie et al., "Structural basis of RIP1 inhibition by necrostatins." Structure, 2013, 21(3), 493-499.

CRYSTALLINE FORMS OF (S)-5-BENZYL-N-(5-METHYL-4-OXO-2,3,4,5-TETRAHYDROPYRIDO [3,2-B][1,4]OXAZEPIN-3-YL)-4H-1,2,4-TRIAZOLE-3-CARBOXAMIDE

CROSS-REFERENCE TO RELATED APPLICATIONS

This application claims the benefit of priority to U.S. provisional application No. 63/298,816, filed Jan. 12, 2022, and U.S. provisional application No. 63/386,113 filed Dec. 5, 2022, each of which is incorporated by reference herein in its entirety for any purpose.

TECHNICAL FIELD

Described herein are crystalline forms of (S)-5-benzyl-N-(5-methyl-4-oxo-2,3,4,5-tetrahydropyrido [3,2-b][1,4] oxazepin-3-yl)-4H-1,2,4-triazole-3-carboxamide, the process of preparing the forms, pharmaceutical compositions, and methods of use thereof.

BACKGROUND

Receptor-interacting protein kinase 1 (RIPK1) is a key regulator of inflammation, apoptosis, and necroptosis. RIPK1 has an important role in modulating inflammatory responses mediated by nuclear-factor kappa-light chain enhancer of activated B cells (NF-kB). More recent research has shown that its kinase activity controls necroptosis, a form of necrotic cell death. Further, RIPK1 is part of a pro-apoptotic complex indicating its activity in regulating apoptosis. Dysregulation of receptor-interacting protein kinase 1 signaling can lead to excessive inflammation or cell death. Research suggests that inhibition of RIPK1 is a potential clinical target for diseases involving inflammation or cell death. RIPK1 kinase has emerged as a promising therapeutic target for the treatment of a wide range of human neurodegenerative, autoimmune, and inflammatory diseases.

Compound (I) is a RIPK1 inhibitor and may be useful in the treatment of RIPK1 mediated diseases or disorders. Compound (I) is disclosed in WO2017/136727 (also in U.S. Pat. No. 9,815,850) and has the following structure:

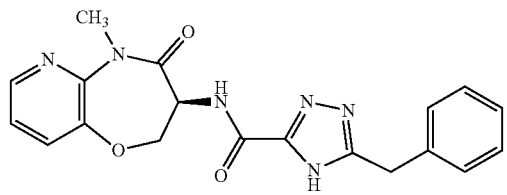 [SMILES: CN1C(=O)[C@@H](NC(=O)c2nnc(Cc3ccccc3)[nH]2)COc2cccnc21]

Solid forms (e.g., crystalline forms) of bioactive compounds, such as Compound (I), are of interest in the pharmaceutical industry, where solid forms with specific physical, chemical, or pharmaceutical properties, such as solubility, dissociation, true density, dissolution, melting point, morphology, compaction behavior, particle size, flow properties, or solid-state stability, may be desirable or even required for pharmaceutical development. Although it is known that the preparation of crystalline forms may improve the physical or pharmaceutical properties of a pharmaceutically active compound, it is not possible to predict whether a compound exists in crystalline form(s) or which crystalline form(s) may possess advantages for a particular purpose prior to the actual preparation and characterization of the crystalline form. In particular, such advantages, in a non-limiting manner could include better processability, solubility or shelf-life stability, just to name a few. Other advantages may also include biological properties such as improved bioavailability, reduced adverse reactions at the GI tract (for example irritation of the GI tract, partial degradation of the compound, etc.), or better deliverability of the drug to the intended target site among other advantages.

SUMMARY

The present disclosure relates to various solid state forms of the RIPK1 inhibitor (S)-5-benzyl-N-(5-methyl-4-oxo-2,3,4,5-tetrahydropyrido [3,2-b][1,4]oxazepin-3-yl)-4H-1,2,4-triazole-3-carboxamide (also referred as Compound (I)), the process of preparing the forms, and pharmaceutical compositions and methods of use thereof.

The present disclosure provides a crystalline form of Compound (I), characterized as Form A.

The present disclosure provides a crystalline form of Compound (I), characterized as Form B.

The present disclosure provides a crystalline form of Compound (I), characterized as Form C.

The present disclosure provides a crystalline form of Compound (I), characterized as Form D.

The present disclosure provides a crystalline form of Compound (I), characterized as Form E.

The present disclosure provides a crystalline form of Compound (I), characterized as Form F.

The crystalline Form B of Compound (I) has high melting point and is less hygroscopic and appears to be most suitable for industrial use and storage.

BRIEF DESCRIPTION DRAWINGS

Figure 13:
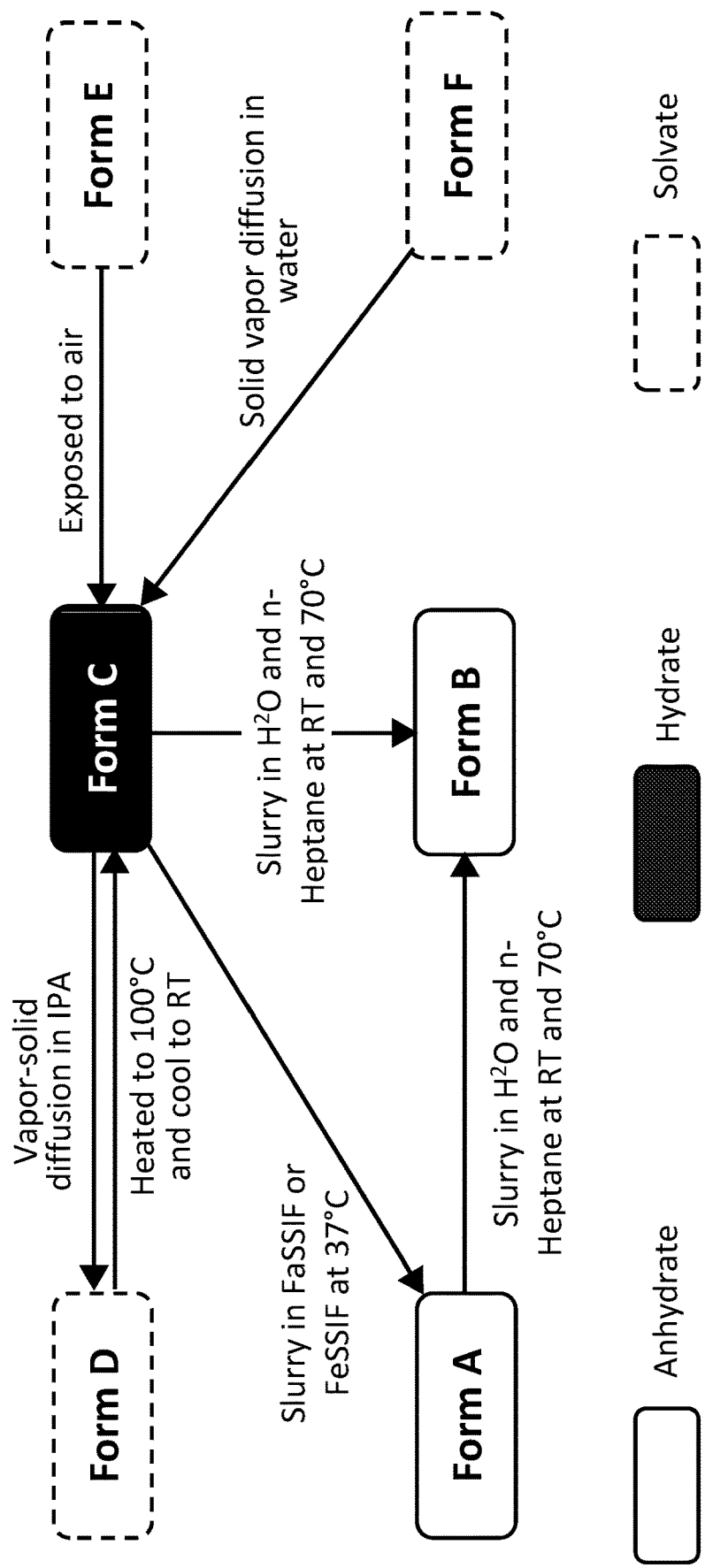

FIG. 13 Inter-conversion relationship between different forms.

Figure 14:
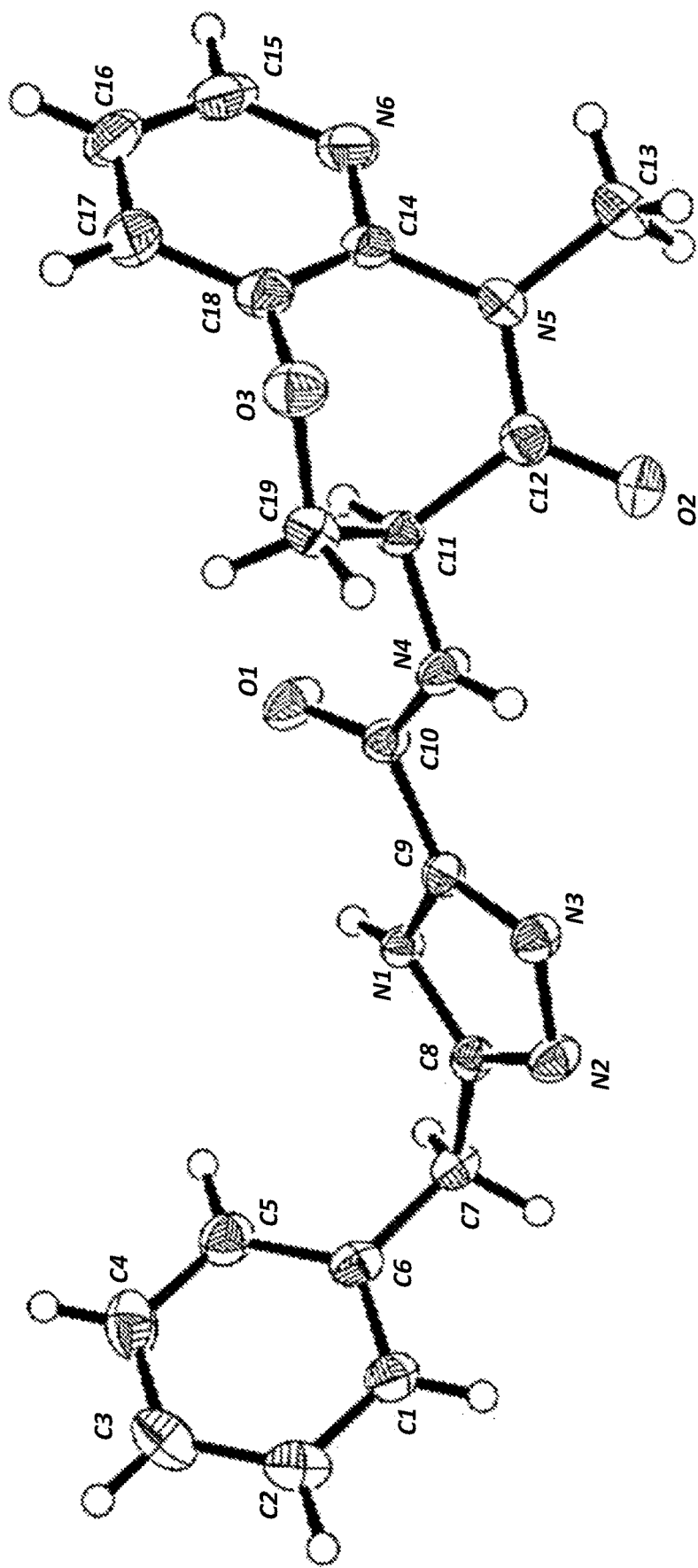

FIG. 14 is thermal ellipsoids drawing of the single crystal of crystalline Form B of Compound (I).

Figure 15:
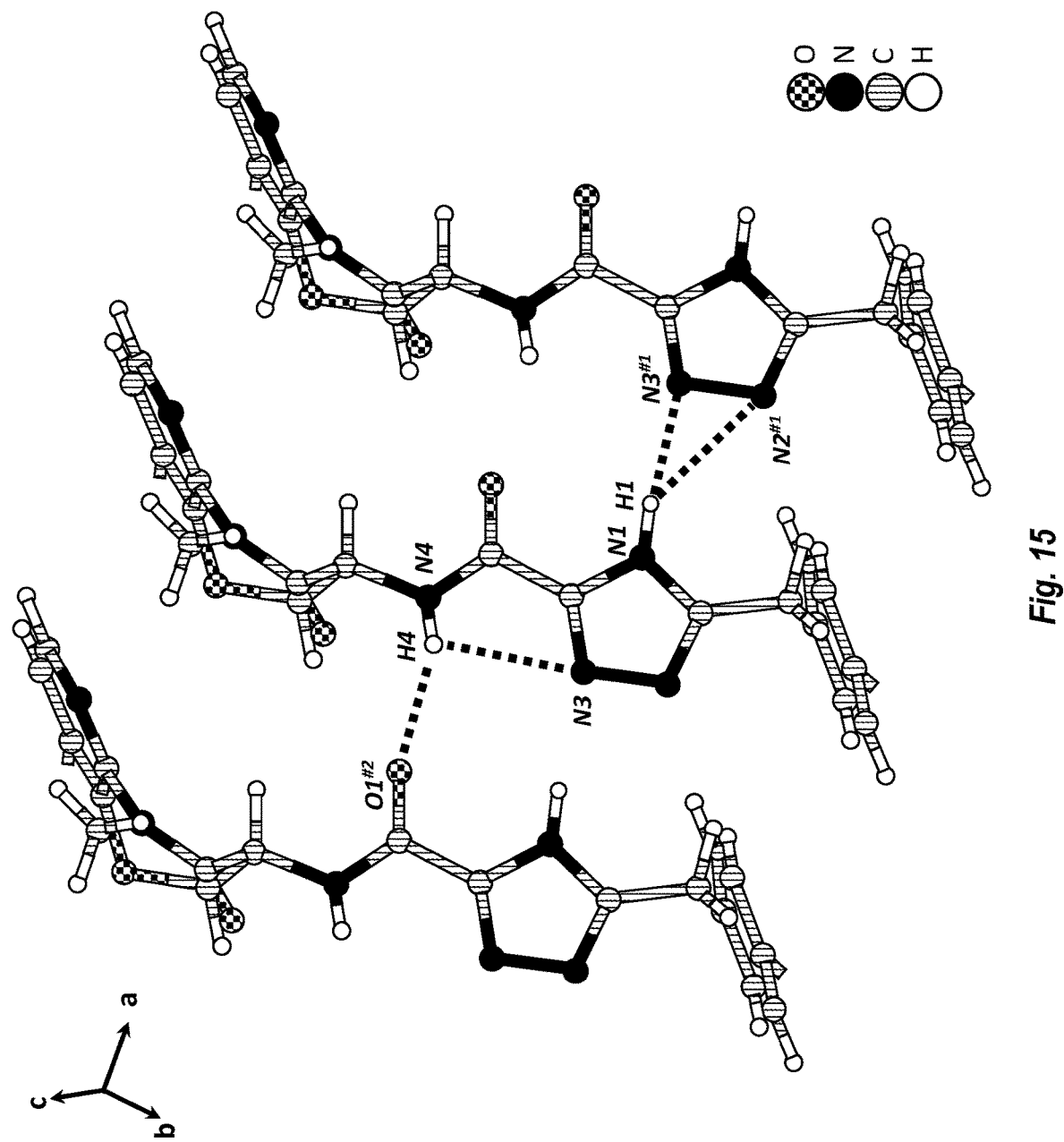

FIG. 15 is the hydrogen bonds in the single crystal structure of crystalline Form B of Compound (I).

Figure 16:
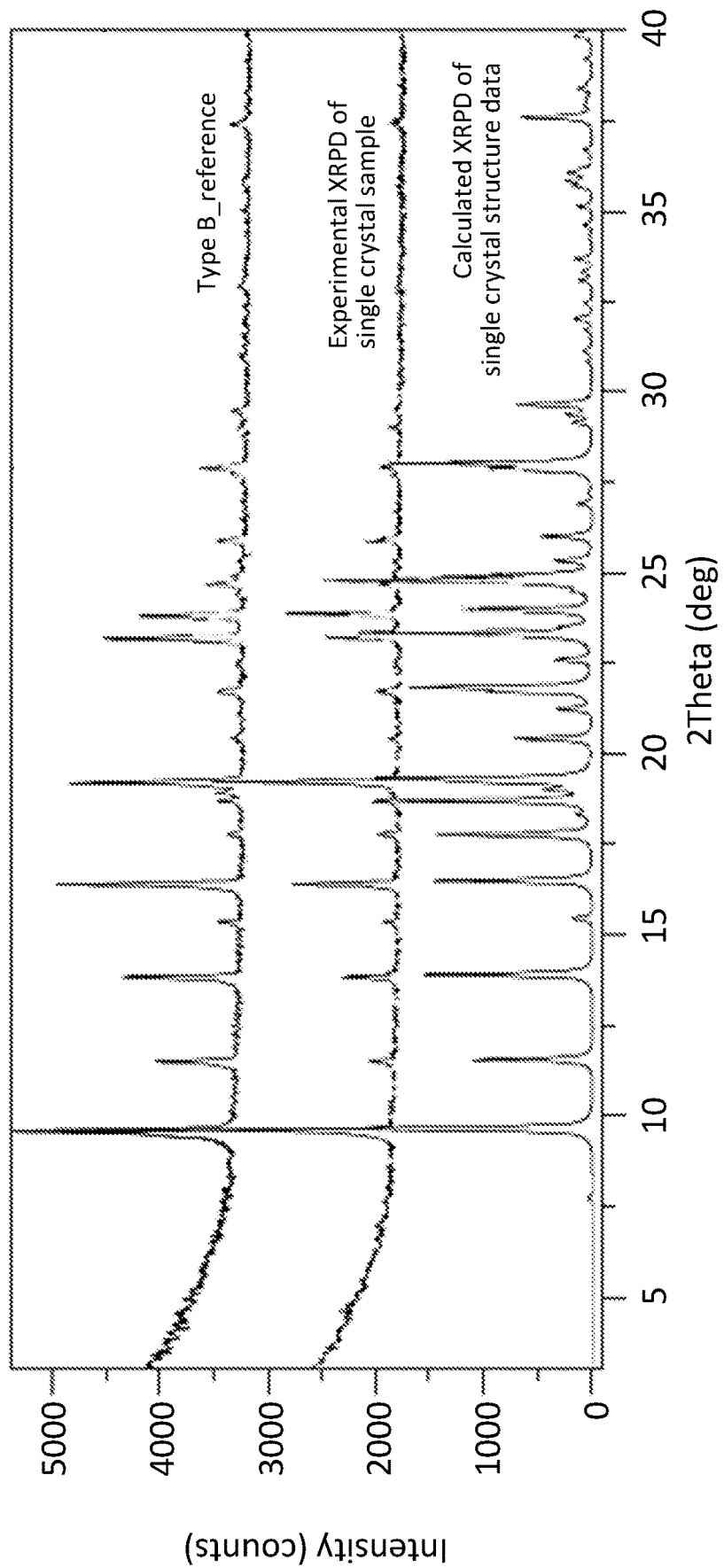

FIG. 16 is the calculated XRPD generated from the single crystal structure of crystalline Form B of Compound (I).

Figure 17:
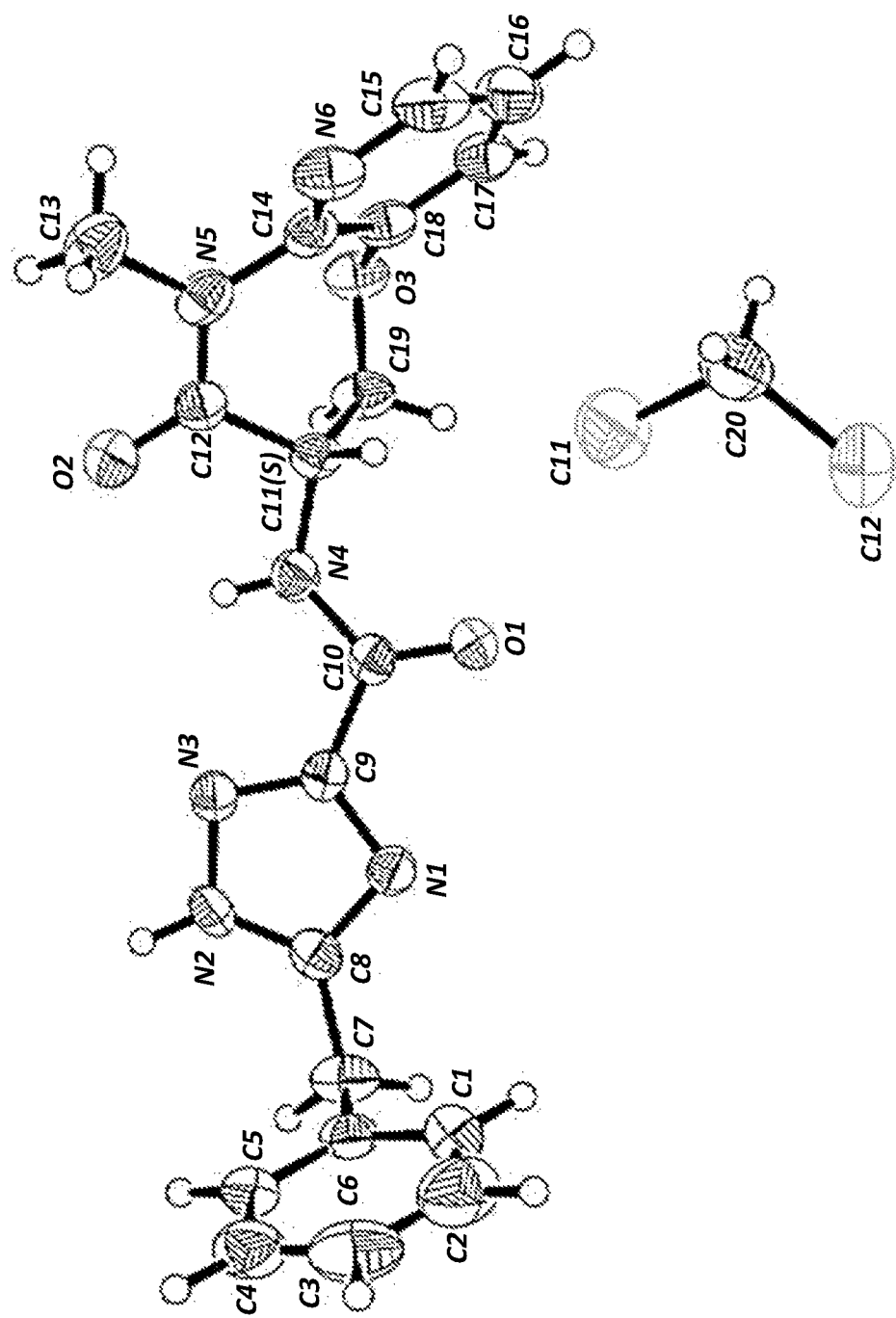

FIG. 17 is thermal ellipsoids drawing of the single crystal of crystalline Form E of Compound (I).

Figure 18:
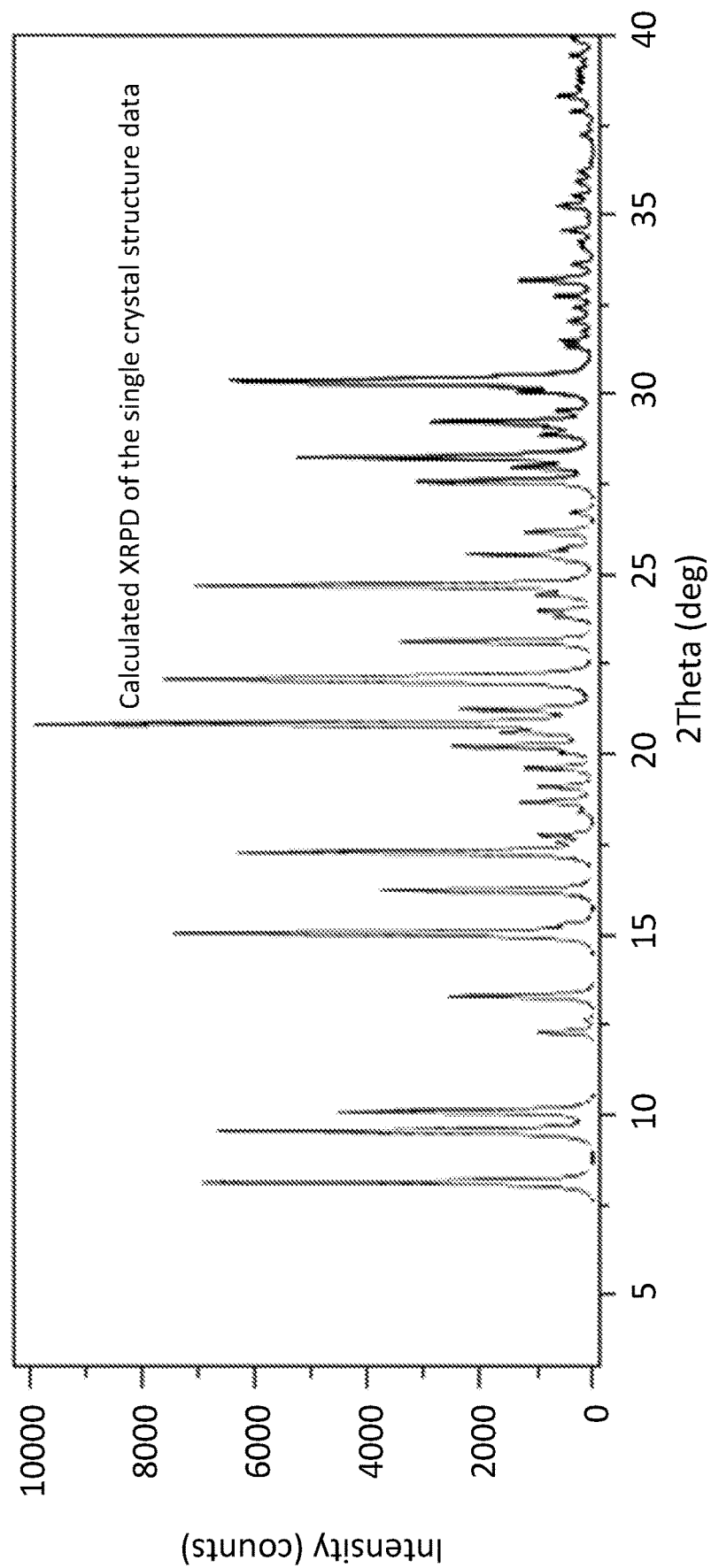

FIG. 18 is the calculated XRPD generated from the single crystal structure of crystalline Form E of Compound (I).

DETAILED DESCRIPTION

The details of the disclosure are set forth in the accompanying description below. Although methods and materials similar or equivalent to those described herein can be used in the practice or testing of the present disclosure, illustrative methods and materials are now described. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs.

The present disclosure provides crystalline solid forms of Compound (I). The present disclosure also provides pharmaceutical compositions comprising one or more crystalline solid forms of Compound (I). The disclosure also provides processes for making the crystalline solid forms, and methods for using them.

Herein are also provided pharmaceutical compositions comprising one or more compounds selected from the group consisting of Form A of Compound (I), Form B of Compound (I), Form C of Compound (I), Form D of Compound (I), Form E of Compound (I), and Form F of Compound (I)); and a pharmaceutically acceptable excipient.

Herein are also provided methods of preparing pharmaceutical compositions comprising mixing one or more compounds selected from the group consisting of Form A of Compound (I), Form B of Compound (I), Form C of Compound (I), Form D of Compound (I), Form E of Compound (I), and Form F of Compound (I)); and a pharmaceutically acceptable excipient.

Herein are also provided methods of preparing pharmaceutical compositions comprising mixing Form B of Compound (I) and a pharmaceutically acceptable excipient.

Herein are also provided methods of treating a disease associated with RIPK1 in a patient in need thereof, comprising administering to the patient an effective amount of one or more compounds selected from the group consisting of Form A of Compound (I), Form B of Compound (I), Form C of Compound (I), Form D of Compound (I), Form E of Compound (I), and Form F of Compound (I)).

Herein are also provided methods of treating a disease associated with RIPK1 in a patient in need thereof, comprising administering to the patient an effective amount of a pharmaceutical composition comprising one or more compounds selected from the group consisting of Form A of Compound (I), Form B of Compound (I), Form C of Compound (I), Form D of Compound (I), Form E of Compound (I), and Form F of Compound (I)).

Herein are also provided methods of inhibiting RIPK1. The method comprises administering to a patient in need thereof, an effective amount of one or more compounds selected from the group consisting of Form A of Compound (I), Form B of Compound (I), Form C of Compound (I), Form D of Compound (I), Form E of Compound (I), and Form F of Compound (I)).

Herein are also provided methods of inhibiting RIPK1 comprising administering to a patient in need thereof, an effective amount of a pharmaceutical composition comprising one or more compounds selected from the group consisting of Form A of Compound (I), Form B of Compound (I), Form C of Compound (I), Form D of Compound (I), Form E of Compound (I), and Form F of Compound (I)).

Another aspect of the disclosure relates to one or more compounds selected from the group consisting of Form A of Compound (I), Form B of Compound (I), Form C of Compound (I), Form D of Compound (I), Form E of Compound (I), and Form F of Compound (I)), for use in treating a disease associated with RIPK1. One aspect of the disclosure relates to pharmaceutical compositions comprising one or more compounds selected from the group consisting of Form A of Compound (I), Form B of Compound (I), Form C of Compound (I), Form D of Compound (I), Form E of Compound (I), and Form F of Compound (I)); and a pharmaceutically acceptable excipient, for use in treating a disease or disorder associated with RIPK1.

Herein is also provided the use of one or more compounds selected from the group consisting of Form A of Compound (I), Form B of Compound (I), Form C of Compound (I), Form D of Compound (I), Form E of Compound (I), and Form F of Compound (I)), in the manufacture of a medicament for treating a disease associated with RIPK1. Another aspect of the disclosure relates to the use of pharmaceutical compositions comprising one or more compounds selected from the group consisting of Form A of Compound (I), Form B of Compound (I), Form C of Compound (I), Form D of Compound (I), Form E of Compound (I), and Form F of Compound (I)); and a pharmaceutically acceptable excipient, in the manufacture of a medicament for treating a disease or disorder associated with RIPK1.

Herein is also provided one or more compounds selected from the group consisting of Form A of Compound (I), Form B of Compound (I), Form C of Compound (I), Form D of Compound (I), Form E of Compound (I), and Form F of Compound (I)), for use as a medicament. Another aspect of the disclosure relates to pharmaceutical compositions comprising one or more compounds selected from the group consisting of Form A of Compound (I), Form B of Compound (I), Form C of Compound (I), Form D of Compound (I), Form E of Compound (I), and Form F of Compound (I)), for use as a medicament. In some embodiments, the medicament is used for treating a disease or disorder mediated by RIPK1.

Provided herein is a method of treating a receptor-interacting protein kinase 1-mediated disease or disorder comprising administering a therapeutically effective amount of a compound or pharmaceutical composition disclosed herein to a patient in need thereof.

In certain embodiments, the disease or disorder is inflammatory bowel disease, Crohn's disease, ulcerative colitis, psoriasis, retinal detachment, retinitis pigmentosa, macular degeneration, pancreatitis, atopic dermatitis, rheumatoid arthritis, spondyloarthritis, gout, SoJIA, systemic lupus erythematosus, cutaneous lupus erythematosus, Sjogren's syndrome, systemic scleroderma, anti-phospholipid syndrome, vasculitis, osteoarthritis, non-alcohol steatohepatitis, alcohol steatohepatitis, autoimmune hepatitis, autoimmune hepatobiliary diseases, primary sclerosing cholangitis, nephritis, Celiac disease, autoimmune ITP, transplant rejection, ischemia reperfusion injury of solid organs, sepsis, systemic inflammatory response syndrome, cytokine release syndrome, covid-19 infection, cerebrovascular accident, myocardial infarction, Huntington's disease, Parkinson's disease, allergic diseases, asthma, atopic dermatitis, multiple sclerosis, type I diabetes, Wegener's granulomatosis, pulmonary sarcoidosis, Behcet's disease, interleukin-1 converting enzyme associated fever syndrome, chronic obstructive pulmonary disease, tumor necrosis factor receptor-associated periodic syndrome, or peridontitis.

In certain embodiments, the disease or disorder is trauma, ischemia, stroke, cardiac infarction, infection, lysosomal storage disease, Gaucher's disease, Krabbe disease, Niemann-Pick disease, sepsis, Parkinson's disease, amyotrophic lateral sclerosis (ALS/Lou Gehrig's Disease), Huntington's disease, HIV-associated dementia, retinal degenerative disease, glaucoma, age-related macular degeneration, rheumatoid arthritis, psoriasis, psoriatic arthritis or inflammatory bowel disease.

In certain embodiments, the disease or disorder is ALS, Friedreich's ataxia, Huntington's disease, Lewy body disease, Parkinson's disease, or spinal muscular atrophy. In certain embodiments, the disease or disorder is brain injury, spinal cord injury, dementia, stroke, ALS, Parkinson's disease, Huntington's disease, multiple sclerosis, diabetic neuropathy, poly glutamine (polyQ) diseases, stroke, Fahr disease, Menke's disease, Wilson's disease, cerebral ischemia, or a prion disorder.

The present disclosure also provides compounds and pharmaceutical compositions that are useful in inhibiting RIPK1.

Each embodiment described herein may be taken alone or in combination with any one or more other embodiments.

Terms

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

The terms "article of manufacture" and "kit" are used as synonyms.

A "pharmaceutically acceptable excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable excipient" as used in the specification and claims includes both one and more than one such excipient.

As used herein, the term "crystalline" or "crystalline solid form," refers to a solid form which is substantially free of any amorphous solid-state form. In some embodiments, the crystalline solid form is a single solid-state form, e.g., crystalline Form A.

In some embodiments, "substantially free" means less than about 10% w/w, less than about 9% w/w, less than about 8% w/w, less than about 7% w/w, less than about 6% w/w, less than about 5% w/w, less than about 4% w/w, less than about 3% w/w, less than about 2.5% w/w, less than about 2% w/w, less than about 1.5% w/w, less than about 1% w/w, less than about 0.75% w/w, less than about 0.50% w/w, less than about 0.25% w/w, less than about 0.10% w/w, or less than about 0.05% w/w of other crystalline forms of the compound and the amorphous compound. In some embodiments, "substantially free" means an undetectable amount of other crystalline forms of the compound and the amorphous compound.

As used herein, the term "substantially pure" means that the crystalline form contains at least 90 percent, preferably at least 95 percent, more preferably at least 97 percent, and most preferably at least 99 percent by weight of the indicated crystalline form compared to the total weight of the compound of all forms.

Alternatively, it will be understood that "substantially pure" means that the crystalline form contains less than 10 percent, preferably less than 5 percent, more preferably less than 3 percent, and most preferably less than 1 percent by weight of impurities, including other polymorphic, solvated or amorphous forms compared to the total weight of the compound of all forms.

An "XRPD pattern" or "X-ray powder diffraction pattern" is an x-y graph with diffraction angle (i.e., ° 2θ) on the x-axis and intensity on the y-axis. The peaks within this pattern may be used to characterize a crystalline solid form. As with any data measurement, there is variability in XRPD data. The data are often represented solely by the diffraction angle of the peaks rather than including the intensity of the peaks because peak intensity can be particularly sensitive to sample preparation (for example, particle size, moisture content, solvent content, and preferred orientation effects influence the sensitivity), so samples of the same material prepared under different conditions may yield slightly different patterns; this variability is usually greater than the variability in diffraction angles. Diffraction angle variability may also be sensitive to sample preparation. Other sources of variability come from instrument parameters and processing of the raw X-ray data: different X-ray instruments operate using different parameters and these may lead to slightly different XRPD patterns from the same solid form, and similarly different software packages process X-ray data differently and this also leads to variability. These and other sources of variability are known to t hose of ordinary skill in the pharmaceutical arts. Due to such sources of variability, it is usual to assign a variability of about ±0.2° θ to diffraction angles in XRPD patterns.

Solid Forms

Forms A and B are anhydrous polymorphs of Compound (I). Form C is a hydrate of Compound (I), and Form D, Form E and Form, F are solvates of Compound (I).

The preparation and uses of Compound (I) have been previously described (see WO 2017/136727, U.S. Pat. No. 9,815,850).

In some embodiments provided herein, Compound (I) is crystalline.

In some embodiments, the crystallinity of a solid form is characterized by X-Ray Powder Diffraction (XRPD).

In some embodiments, the crystallinity of a solid form is determined by thermo gravimetric analysis (TGA).

In some embodiments, the crystallinity of a solid form is determined by differential scanning calorimeter (DSC).

Herein is provided a crystalline form selected from the group consisting of:

Form A of (S)-5-benzyl-N-(5-methyl-4-oxo-2,3,4,5-tetrahydropyrido [3,2-b][1,4]oxazepin-3-yl)-4H-1,2,4-triazole-3-carboxamide;

Form B of (S)-5-benzyl-N-(5-methyl-4-oxo-2,3,4,5-tetrahydropyrido [3,2-b][1,4]oxazepin-3-yl)-4H-1,2,4-triazole-3-carboxamide;

Form C of (S)-5-benzyl-N-(5-methyl-4-oxo-2,3,4,5-tetrahydropyrido [3,2-b][1,4]oxazepin-3-yl)-4H-1,2,4-triazole-3-carboxamide;

Form D of (S)-5-benzyl-N-(5-methyl-4-oxo-2,3,4,5-tetrahydropyrido [3,2-b][1,4]oxazepin-3-yl)-4H-1,2,4-triazole-3-carboxamide;

Form E of (S)-5-benzyl-N-(5-methyl-4-oxo-2,3,4,5-tetrahydropyrido [3,2-b][1,4]oxazepin-3-yl)-4H-1,2,4-triazole-3-carboxamide; and Form F of (S)-5-benzyl-N-(5-methyl-4-oxo-2,3,4,5-tetrahydropyrido [3,2-b][1,4]oxazepin-3-yl)-4H-1,2,4-triazole-3-carboxamide.

Herein is provided crystalline Form A of Compound (I).

Figure 1:
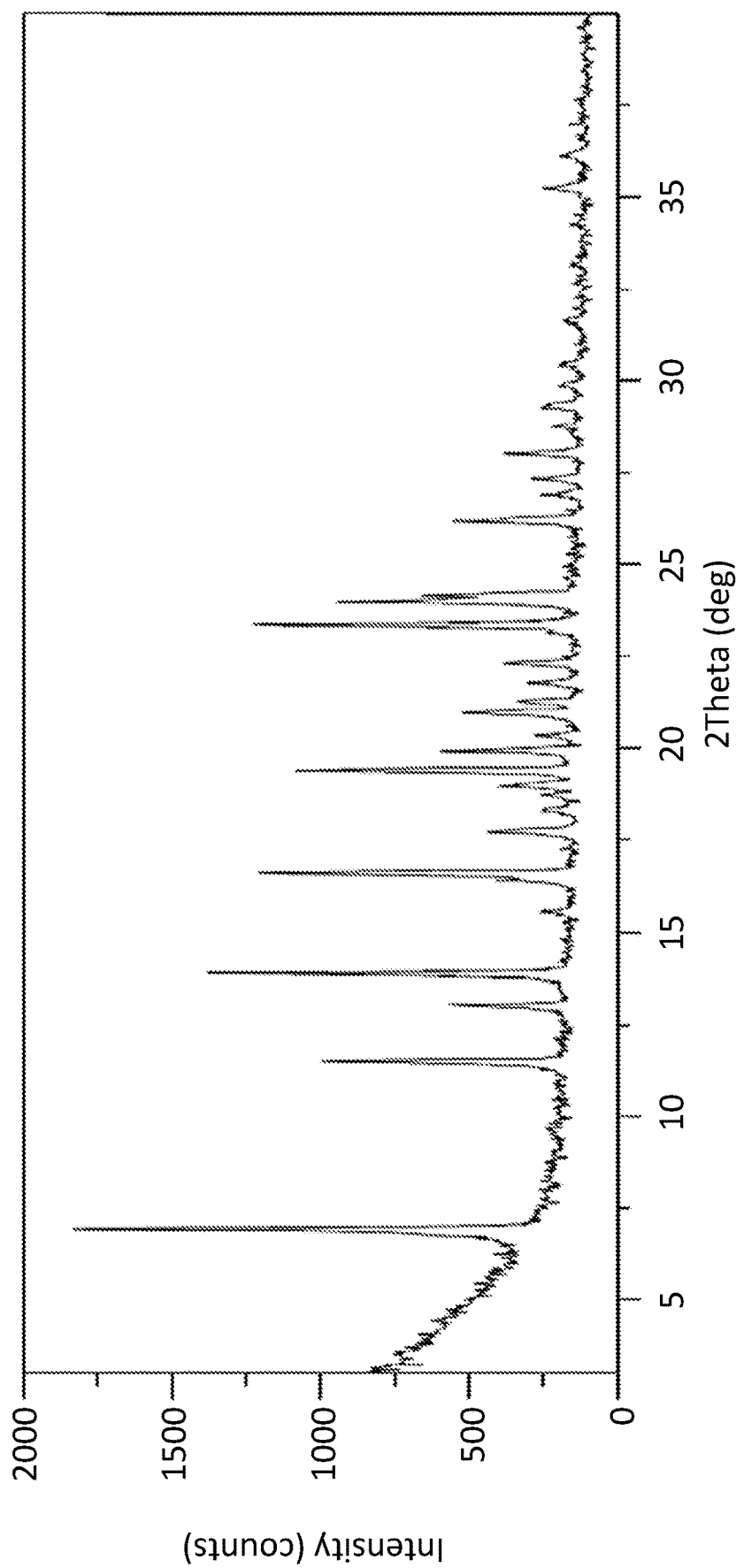
FIG. 1 is an X-ray powder diffractogram of crystalline Form A of Compound (I).
Figure 2:
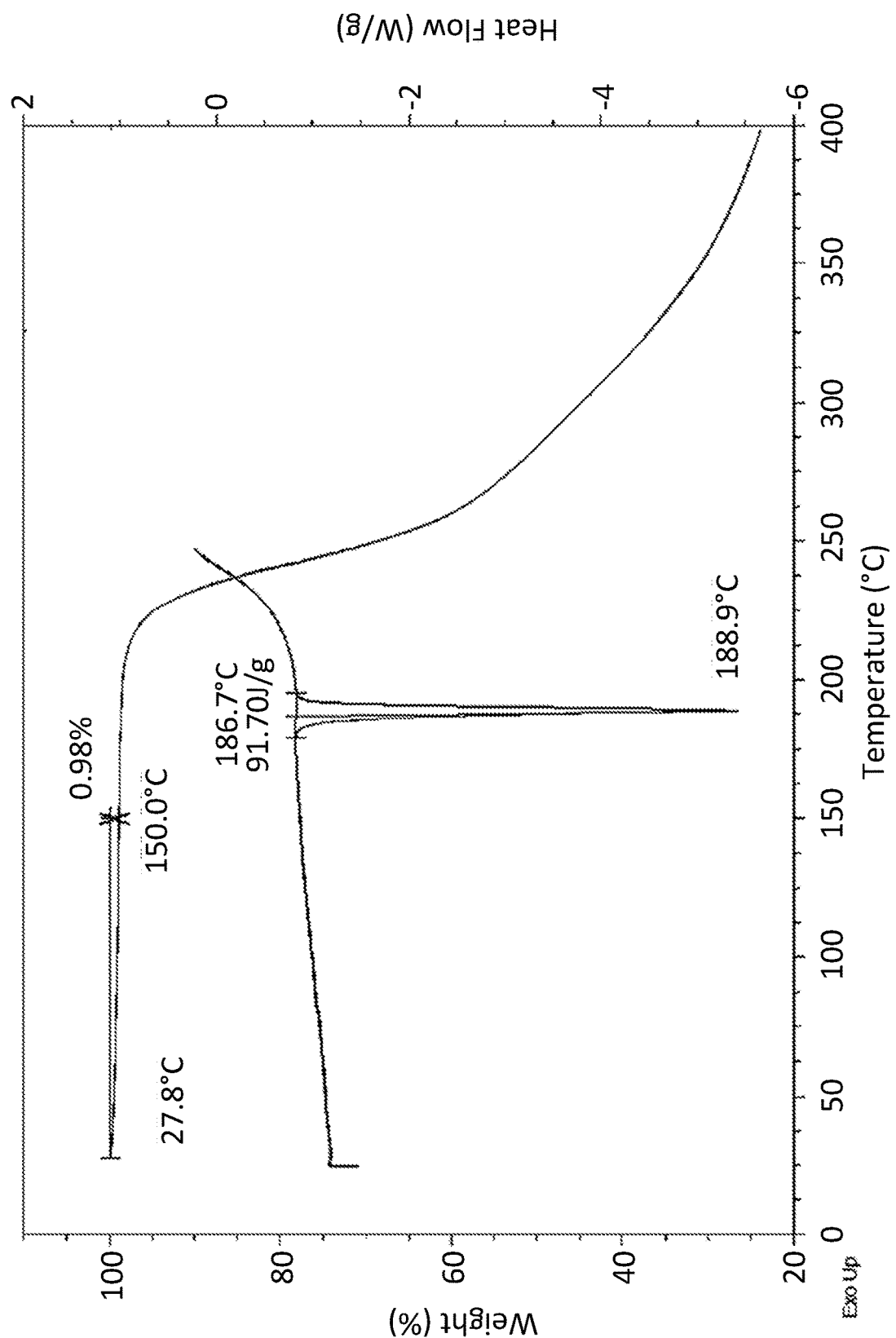
FIG. 2 is a Differential Scanning Calorimetry/Thermal Gravimetric Analysis (DSC/TGA) thermogram of crystalline Form A of Compound (I).

In some embodiments, crystalline Form A of Compound (I) is characterized as having one or more of:
  a) an X-ray powder diffraction (XRPD) pattern substantially the same as shown in FIG. 1;
  b) an X-ray powder diffraction (XRPD) pattern derived using Cu (Kα) radiation with peaks, in term of 2-theta degrees, at about 6.9, 13.0, 16.6, and 23.4±0.2 degrees;
  c) a Differential Scanning Calorimetry (DSC) thermogram substantially the same as shown in FIG. 2;
  d) a Differential Scanning Calorimetry (DSC) thermogram with three endothermic events having an onset at about 186.7° C. and a peak at about 188.9° C.;
  e) a Thermogravimetric Analysis (TGA) pattern substantially the same as shown in FIG. 2;
  f) a Thermogravimetric Analysis (TGA) pattern with an about 1.0% w/w loss from about 27.8° C. to about 150° C.; or
  g) combinations thereof.

In one embodiment, the crystalline Form A of Compound (I), having an X-ray powder diffraction pattern derived using Cu (Kα) radiation comprising one, two, three, four, five, six, seven or more peaks selected from the group consisting of: 6.9, 11.5, 13.0, 13.9, 16.6, 19.4, 23.4, and 24.0 (expressed in degrees 2-theta±0.2 degrees 2-theta).

In one embodiment, the crystalline Form A of Compound (I), having an X-ray powder diffraction pattern derived using Cu (Kα) radiation comprising one peak selected from the group consisting of: 6.9, 11.5, 13.0, 13.9, 16.6, 19.4, 23.4, and 24.0 (expressed in degrees 2-theta±0.2 degrees 2-theta).

In one embodiment, the crystalline Form A of Compound (I), having an X-ray powder diffraction pattern derived using Cu (Kα) radiation comprising two peaks selected from the group consisting of: 6.9, 11.5, 13.0, 13.9, 16.6, 19.4, 23.4, and 24.0 (expressed in degrees 2-theta±0.2 degrees 2-theta).

In one embodiment, the crystalline Form A of Compound (I), having an X-ray powder diffraction pattern derived using Cu (Kα) radiation comprising three peaks selected from the group consisting of: 6.9, 11.5, 13.0, 13.9, 16.6, 19.4, 23.4, and 24.0 (expressed in degrees 2-theta±0.2 degrees 2-theta).

In one embodiment, the crystalline Form A of Compound (I), having an X-ray powder diffraction pattern derived using Cu (Kα) radiation comprising four peaks selected from the group consisting of: 6.9, 11.5, 13.0, 13.9, 16.6, 19.4, 23.4, and 24.0 (expressed in degrees 2-theta±0.2 degrees 2-theta).

In one embodiment, the crystalline Form A of Compound (I), having an X-ray powder diffraction pattern derived using Cu (Kα) radiation comprising five peaks selected from the group consisting of: 6.9, 11.5, 13.0, 13.9, 16.6, 19.4, 23.4, and 24.0 (expressed in degrees 2-theta±0.2 degrees 2-theta).

In one embodiment, the crystalline Form A of Compound (I), having an X-ray powder diffraction pattern derived using Cu (Kα) radiation comprising six peaks selected from the group consisting of: 6.9, 11.5, 13.0, 13.9, 16.6, 19.4, 23.4, and 24.0 (expressed in degrees 2-theta±0.2 degrees 2-theta).

In one embodiment, the crystalline Form A of Compound (I), having an X-ray powder diffraction pattern derived using Cu (Kα) radiation comprising seven or more peaks selected from the group consisting of: 6.9, 11.5, 13.0, 13.9, 16.6, 19.4, 23.4, and 24.0 (expressed in degrees 2-theta±0.2 degrees 2-theta).

In one embodiment, the crystalline Form A of Compound (I), having an X-ray powder diffraction pattern comprising a peak, in terms of 2-theta degree, at about 6.9 (each time plus or minus 0.2).

In one embodiment, the crystalline Form A of Compound (I), having an X-ray powder diffraction pattern comprising a peak, in term of 2-theta degree, at about 6.9 and about 13.0 (each time plus or minus 0.2).

In one embodiment, the crystalline Form A of Compound (I) having one or more X-ray powder diffraction displaying peaks expressed as degree 2-Theta degrees at about 6.9, 13.0, 16.6 and 23.4 (each time plus or minus 0.2).

In one embodiment, the crystalline Form A of Compound (I), having the X-ray powder diffraction pattern comprises one or more 2-theta degrees selected from the group comprising about 13.9, 16.6, 19.4, and 23.4 (each time plus or minus 0.2).

In one embodiment, the crystalline Form A of Compound (I), having an X-ray powder diffraction pattern is substantially in accordance with that shown in FIG. 1.

Herein is also provided a crystalline Form A of Compound (I), characterized by a differential scanning calorimetry (DSC) curve with an onset at about 186.7° C. and an endothermic peak at 188.9° C.

Herein are also provided processes for the preparation of the crystalline Form A of Compound (I) comprising at least the following steps:
  a) dissolving Compound (I) in a solvent selected from CPME, EtOH, IPA, Acetone, MIBK, EtOAc, IPAc, ACN, MTBE, THF, n-Heptane, MeOAc, 2-MeTHF and toluene, at a set temperature ranging from 50° C. to 70° C.;
  b) slowly cooling to room temperature;
  c) filtering, washing with the solvent and drying to provide the crystalline Form A of Compound (I) formed in step 2.

Herein is provided a crystalline Form B of Compound (I).

Figure 3:
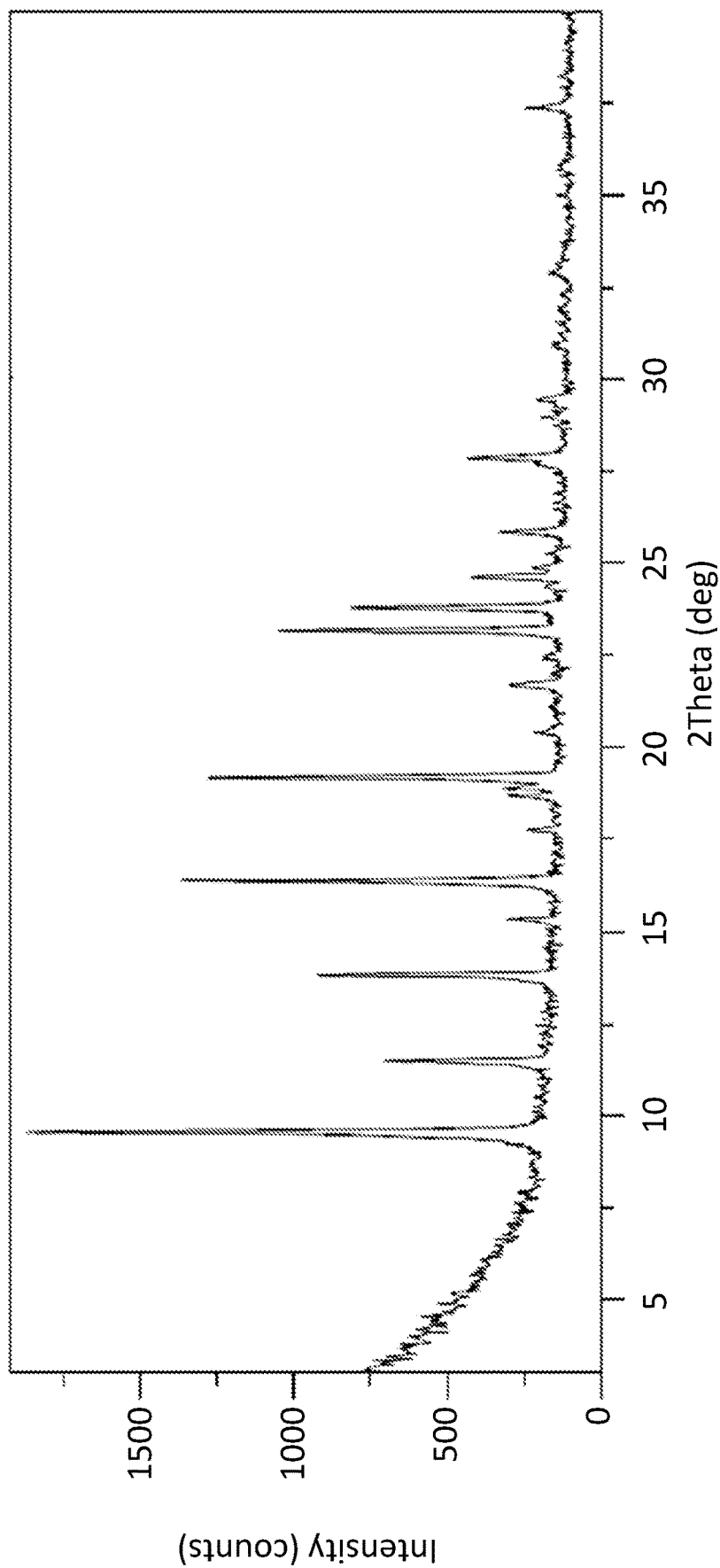
FIG. 3 is an X-ray powder diffractogram of crystalline Form B of Compound (I).
Figure 4:
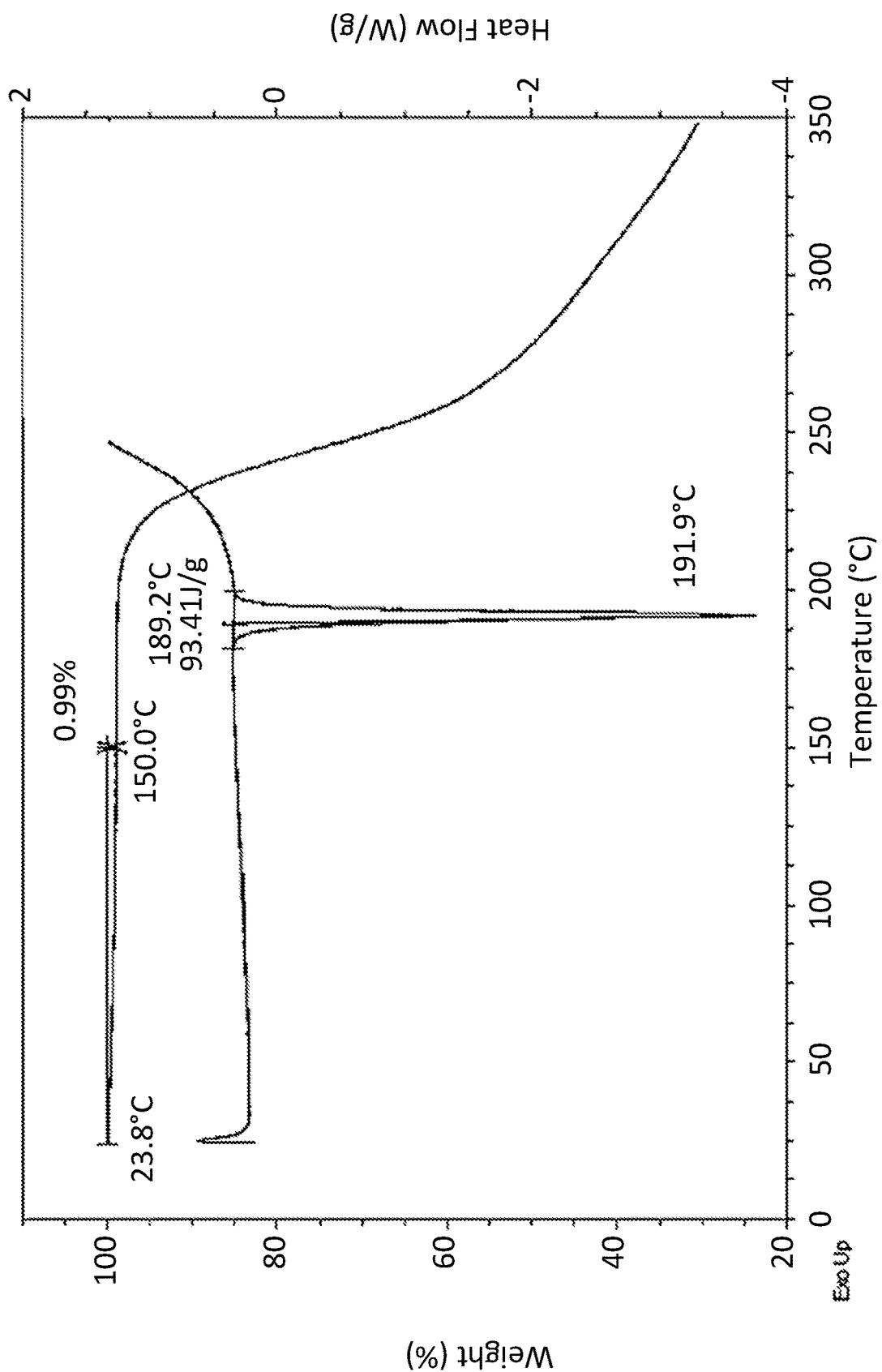
FIG. 4 is a Differential Scanning Calorimetry/Thermal Gravimetric Analysis (DSC/TGA) thermogram of crystalline Form B of Compound (I).

In some embodiments, crystalline Form B of Compound (I) is characterized as having one or more of:
  a) an X-ray powder diffraction (XRPD) pattern substantially the same as shown in FIG. 3;
  b) an X-ray powder diffraction (XRPD) pattern derived using Cu (Kα) radiation with peaks, in term of 2-theta degrees, at about 9.6, 11.5, 16.4, 19.2, and 23.8±0.2 degrees;
  c) unit cell parameters substantially the same as shown in Table 25;
  d) a Differential Scanning Calorimetry (DSC) thermogram substantially the same as shown in FIG. 4;
  e) a Differential Scanning Calorimetry (DSC) thermogram with three endothermic events having an onset at about 189.2° C. and a peak at about 191.9° C.;
  f) a Thermogravimetric Analysis (TGA) pattern substantially the same as shown in FIG. 4; g) a Thermogravimetric Analysis (TGA) pattern with a about 1.0% w/w loss from about 23.8° C. to about 150° C.; or
  h) combinations thereof.

Herein is also provided a crystalline form of Compound (I), characterized as Form B.

In one embodiment, the crystalline Form B of compounds (I) consists of one tautomer.

In one embodiment, the crystalline Form B of compounds (I) having at least 90% (w/w) of one tautomer, wherein hydrogen is on 4-position of triazole ring of the tautomer.

In one embodiment, the crystalline Form B of compounds (I) having at least 95% (w/w) of one tautomer, wherein hydrogen is on 4-position of triazole ring of the tautomer.

In one embodiment, the crystalline Form B of compounds (I) having at least 97% (w/w) of one tautomer, wherein hydrogen is on 4-position of triazole ring of the tautomer.

In one embodiment, the crystalline Form B of Compound (I), having an X-ray powder diffraction pattern derived using Cu (Kα) radiation comprising one, two, three, four, five, six or more peaks selected from the group consisting of: 9.6, 11.5, 13.8, 16.4, 19.2, 23.2, and 23.8 (expressed in degrees 2-theta±0.2 degrees 2-theta).

In one embodiment, the crystalline Form B of Compound (I), having an X-ray powder diffraction pattern derived using Cu (Kα) radiation comprising one peak selected from the group consisting of: 9.6, 11.5, 13.8, 16.4, 19.2, 23.2, and 23.8 (expressed in degrees 2-theta±0.2 degrees 2-theta).

In one embodiment, the crystalline Form B of Compound (I), having an X-ray powder diffraction pattern derived using Cu (Kα) radiation comprising two peaks selected from the group consisting of: 9.6, 11.5, 13.8, 16.4, 19.2, 23.2, and 23.8 (expressed in degrees 2-theta 0.2 degrees 2-theta).

In one embodiment, the crystalline Form B of Compound (I), having an X-ray powder diffraction pattern derived using Cu (Kα) radiation comprising three peaks selected from the group consisting of: 9.6, 11.5, 13.8, 16.4, 19.2, 23.2, and 23.8 (expressed in degrees 2-theta 0.2 degrees 2-theta).

In one embodiment, the crystalline Form B of Compound (I), having an X-ray powder diffraction pattern derived using Cu (Kα) radiation comprising four peaks selected from the group consisting of: 9.6, 11.5, 13.8, 16.4, 19.2, 23.2, and 23.8 (expressed in degrees 2-theta 0.2 degrees 2-theta).

In one embodiment, the crystalline Form B of Compound (I), having an X-ray powder diffraction pattern derived using Cu (Kα) radiation comprising five peaks selected from the group consisting of: 9.6, 11.5, 13.8, 16.4, 19.2, 23.2, and 23.8 (expressed in degrees 2-theta 0.2 degrees 2-theta).

In one embodiment, the crystalline Form B of Compound (I), having an X-ray powder diffraction pattern derived using Cu (Kα) radiation comprising six or more peaks selected from the group consisting of: 9.6, 11.5, 13.8, 16.4, 19.2, 23.2, and 23.8 (expressed in degrees 2-theta±0.2 degrees 2-theta).

Herein is also provided a crystalline Form B of Compound (I), having an X-ray powder diffraction pattern comprising a peak, in term of 2-theta degree, at about 9.6 and about 16.4 (each time plus or minus 0.2).

Herein is also provided a crystalline Form B of Compound (I), having the X-ray powder diffraction displaying one or more peaks expressed as 2-theta degrees at about 9.6, 11.5, 16.4, 19.2, 23.2 and 23.8 (each time plus or minus 0.2).

Herein is also provided a crystalline Form B of Compound (I), having the X-ray powder diffraction pattern comprises one or more 2-theta degrees selected from the group comprising about 11.5, 19.2, 23.2, and 23.8 (each time plus or minus 0.2).

Herein is also provided a crystalline Form B of Compound (I), having an X-ray powder diffraction pattern is substantially in accordance with that shown in FIG. 3.

Herein is also provided a crystalline Form B of Compound (I), having cell parameters substantially the same as: a=5.0418(8) Å, b=15.320(3) Å, c=11.599(2) Å, α=90°, β=98.383(5)°, γ=90°, V=886.3(3) Å$^3$.

Herein is also provided a crystalline Form B of Compound (I), having cell parameters substantially the same as: a=5.0418 Å, b=15.320 Å, c 11.599 Å, =90°, β=98.383°, γ=90°, V=886.3 Å$^3$.

Herein is also provided a crystalline Form B of Compound (I), having cell parameters substantially the same as: a=5.04 Å, b=15.32 Å, c=11.60 Å, a=90°, β=98.38°, γ=90°, V=886.33 Å$^3$.

Herein is also provided a crystalline Form B of Compound (I), characterized by a differential scanning calorimetry (DSC) curve comprises an endotherm at about 189.2° C. and an endothermic peak at 191.9° C.

Herein are also provided processes for the preparation of the crystalline Form B of Compound (I) comprising at least the following steps:
a) dissolving Compound (I) in a solvent selected from MIBK, IPAc, H$_2$O and dimethyl carbonate to form a slurry;
b) stirring the slurry at room temperature;
c) filtering, washing with the solvent and drying to provide the crystalline Form B of Compound (I).

Herein are also provided processes for the preparation of the crystalline Form B of Compound (I) comprising at least the following steps:
a) dissolving Compound (I) in a solvent selected from EtOH, IPA, EtOAc, n-PrOAc, IPA/H$_2$O, EtOH/IPAc, MeOH/Toluene, MIBK, IPAc, H$_2$O and dimethyl carbonate to form a slurry;
b) stirring the slurry at room temperature;
c) filtering, washing with the solvent and drying to provide the crystalline Form B of Compound (I).

Herein are also provided processes for the preparation of the crystalline Form B of Compound (I) comprising at least the following steps:
a) dissolving Compound (I) in a solvent selected from IPAc, EtOH, MIBK, EtOAc, H$_2$O, MeOH/IPAc, EtOH/MeOAc and THF/H$_2$O to form a slurry;
b) stirring the slurry at a set temperature ranging from 40° C. to 60° C.;
c) filtering, washing with the solvent and drying to provide the crystalline Form B of Compound (I).

Herein are also provided processes for the preparation of the crystalline Form B of Compound (I) comprising at least the following steps:
a) dissolving Compound (I) in a solvent selected from MIBK, IPAc, H$_2$O and dimethyl carbonate to form a slurry;
b) stirring the slurry at a set temperature ranging from 40° C. to 60° C.;
c) slowly cooling down to 1-10° C.;
d) filtering, washing with the solvent and drying to provide the crystalline Form B of Compound (I).

Herein are also provided processes for the preparation of the crystalline Form B of Compound (I) comprising at least the following steps:
a) dissolving Compound (I) in a mixture of DMAc and H$_2$O to give a suspension;
b) stirring the suspension at a set temperature ranging from 40° C. to 60° C.;
c) filtering, washing with the solvent and drying to provide the crystalline Form B of Compound (I).

Herein are also provided processes for the preparation of the crystalline Form B of Compound (I) comprising at least the following steps:
a) placing Compound (I) in a first container;
b) placing the first container into a second container with MeOH;

c) sealing the second container and keeping the second container at room temperature for 10-16 days;

d) isolating the solid to provide the crystalline Form B of Compound (I).

Herein is provided a crystalline Form C of Compound (I).

Figure 5:
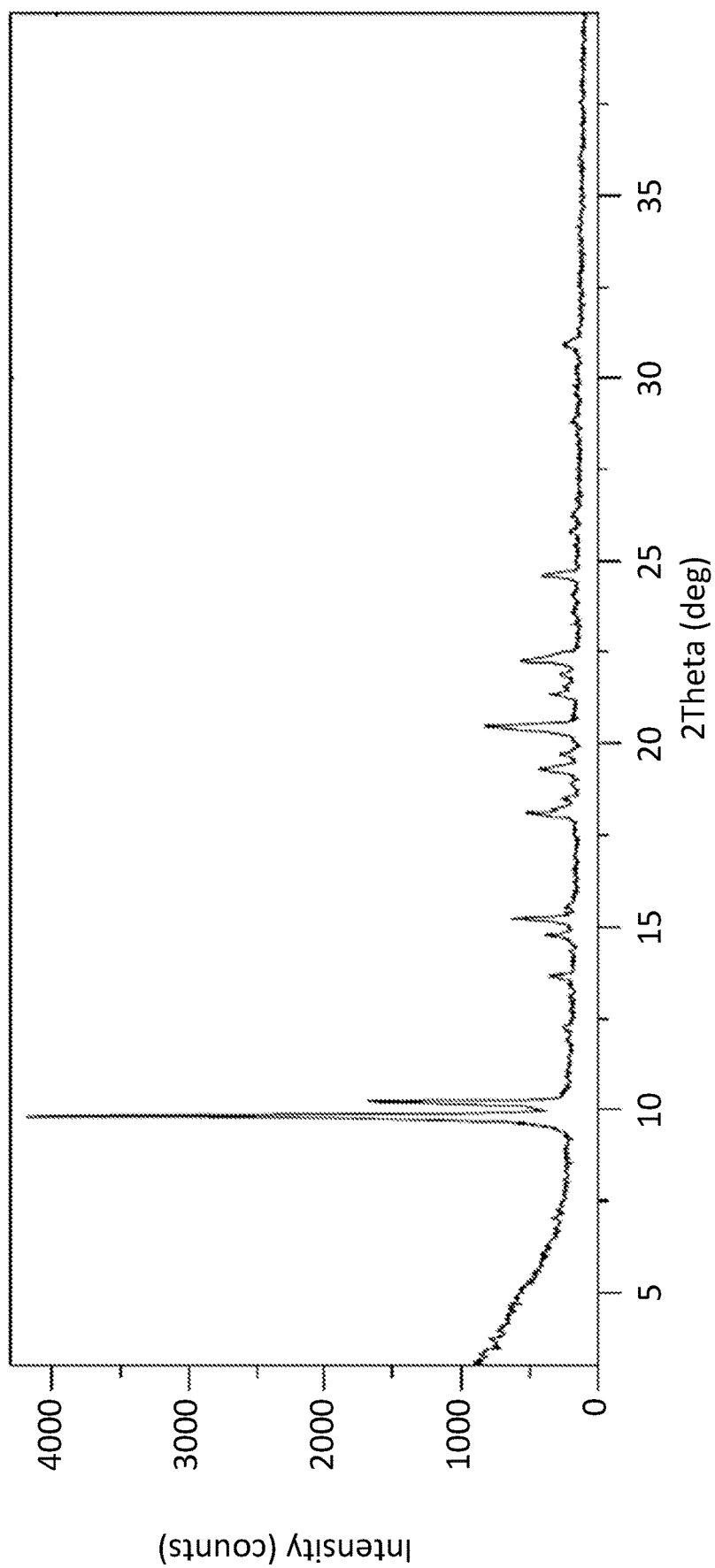
FIG. 5 is an X-ray powder diffractogram of crystalline Form C of Compound (I).
Figure 7:
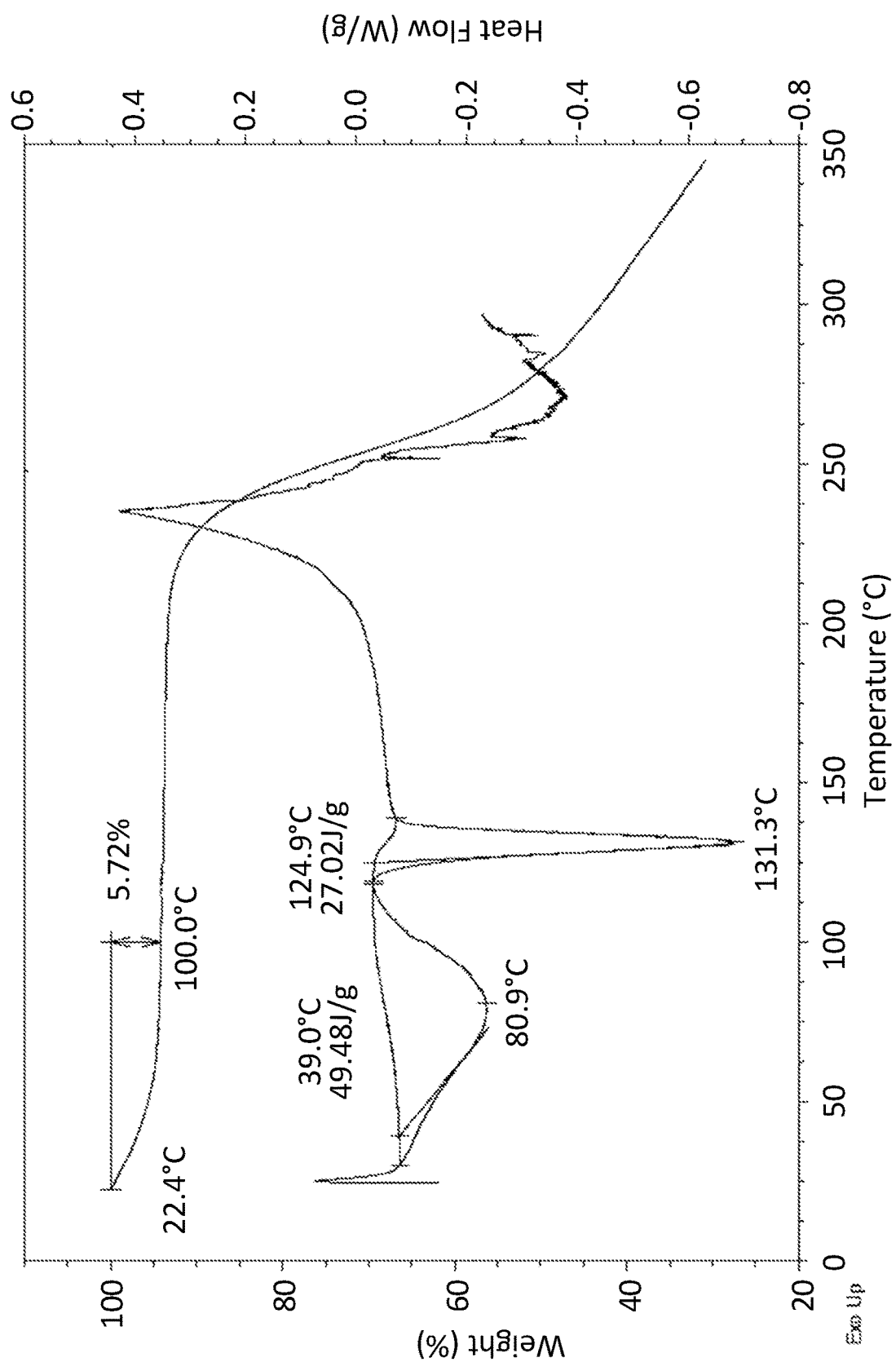
FIG. 7 is a Differential Scanning Calorimetry/Thermal Gravimetric Analysis (DSC/TGA) thermogram of crystalline Form C of Compound (I).

In some embodiments, crystalline Form C of Compound (I) is characterized as having one or more of:
a) an X-ray powder diffraction (XRPD) pattern substantially the same as shown in FIG. 5;
b) an X-ray powder diffraction (XRPD) pattern derived using Cu (Kα) radiation with peaks, in term of 2-theta degrees, at about 9.8, 10.2, 14.8, 15.2, and 20.4±0.2 degrees;
c) a Differential Scanning Calorimetry (DSC) thermogram substantially the same as shown in FIG. 7;
d) a Differential Scanning Calorimetry (DSC) thermogram with three endothermic events having an onset at about 124.9° C. and a peak at about 131.3° C.;
e) a Thermogravimetric Analysis (TGA) pattern substantially the same as shown in FIG. 7;
f) a Thermogravimetric Analysis (TGA) pattern with a about 5.7% w/w loss from about 22.4° C. to about 100° C.; or
g) combinations thereof.

Herein is also provided a crystalline form of Compound (I), characterized as Form C.

In one embodiment, the crystalline Form C of Compound (I), having an X-ray powder diffraction pattern derived using Cu (Kα) radiation comprising three, four, five, six or more peaks selected from the group consisting of: 9.8, 10.2, 14.8, 15.2, 18.1, 20.4, and 22.3 (expressed in degrees 2-theta±0.2 degrees 2-theta).

In one embodiment, the crystalline Form C of Compound (I), having an X-ray powder diffraction pattern derived using Cu (Kα) radiation comprising one peak selected from the group consisting of: 9.8, 10.2, 14.8, 15.2, 18.1, 20.4, and 22.3 (expressed in degrees 2-theta±0.2 degrees 2-theta).

In one embodiment, the crystalline Form C of Compound (I), having an X-ray powder diffraction pattern derived using Cu (Kα) radiation comprising two peaks selected from the group consisting of: 9.8, 10.2, 14.8, 15.2, 18.1, 20.4, and 22.3 (expressed in degrees 2-theta 0.2 degrees 2-theta).

In one embodiment, the crystalline Form C of Compound (I), having an X-ray powder diffraction pattern derived using Cu (Kα) radiation comprising three peaks selected from the group consisting of: 9.8, 10.2, 14.8, 15.2, 18.1, 20.4, and 22.3 (expressed in degrees 2-theta 0.2 degrees 2-theta).

In one embodiment, the crystalline Form C of Compound (I), having an X-ray powder diffraction pattern derived using Cu (Kα) radiation comprising four peaks selected from the group consisting of: 9.8, 10.2, 14.8, 15.2, 18.1, 20.4, and 22.3 (expressed in degrees 2-theta 0.2 degrees 2-theta).

In one embodiment, the crystalline Form C of Compound (I), having an X-ray powder diffraction pattern derived using Cu (Kα) radiation comprising five peaks selected from the group consisting of: 9.8, 10.2, 14.8, 15.2, 18.1, 20.4, and 22.3 (expressed in degrees 2-theta 0.2 degrees 2-theta).

In one embodiment, the crystalline Form C of Compound (I), having an X-ray powder diffraction pattern derived using Cu (Kα) radiation comprising six or more peaks selected from the group consisting of: 9.8, 10.2, 14.8, 15.2, 18.1, 20.4, and 22.3 (expressed in degrees 2-theta±0.2 degrees 2-theta).

Herein is also provided a crystalline Form C of Compound (I), having an X-ray powder diffraction pattern comprising a peak, in term of 2-theta degree, at about 9.8 and about 10.2 (each time plus or minus 0.2).

Herein is also provided a crystalline Form C of Compound (I), having the X-ray powder diffraction pattern comprising a peak, in term of 2-theta degree, selected from the group comprising about 9.8, 10.2, 14.8, 15.2 and 20.4 (each time plus or minus 0.2).

Herein is also provided a crystalline Form C of Compound (I), having the X-ray powder diffraction pattern comprises one or more 2-theta degrees selected from the group comprising about 14.8, 15.2, 18.1, 20.4, and 22.3 (each time plus or minus 0.2).

Herein is also provided a crystalline Form C of Compound (I), having the X-ray powder diffraction pattern is substantially in accordance with that shown in FIG. 5.

Herein is also provided a crystalline Form C of Compound (I), characterized by a differential scanning calorimetry (DSC) curve comprises an endotherm at about 124.9° C. and an endothermic peak at 131.3° C.

Herein are also provided processes for the preparation of the crystalline Form C of Compound (I) comprising at least the following steps:
a) dissolving Compound (I) in MeOH/H₂O to give a slurry;
b) stirring the slurry at a set temperature ranging from 40° C. to 60° C.;
c) slowly cooling down to 1-10° C.;
d) filtering, washing with the solvent and drying to provide the crystalline Form C of Compound (I).

Herein is provided a crystalline Form D of Compound (I).

Figure 9:
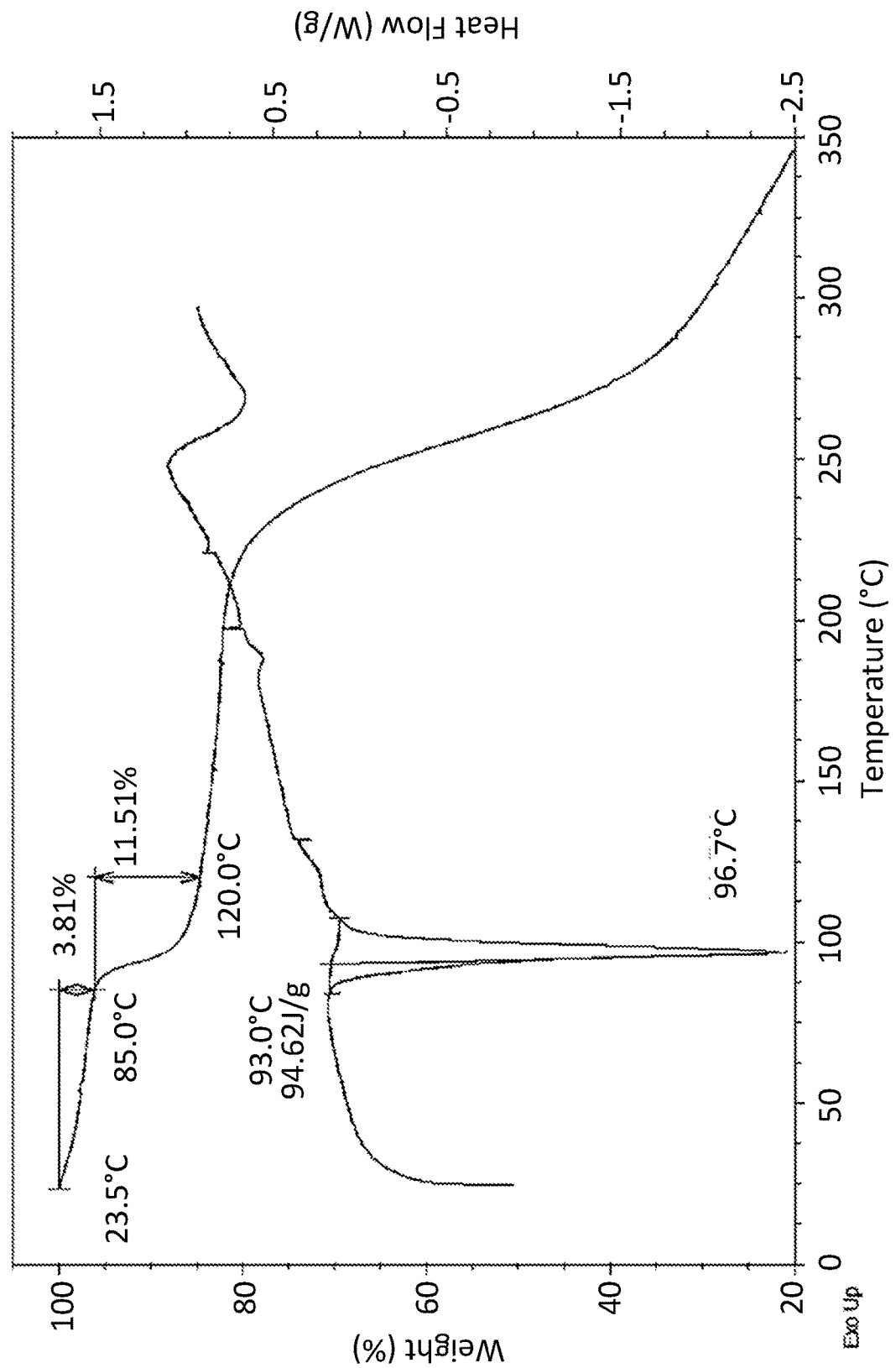
FIG. 9 is a Differential Scanning Calorimetry/Thermal Gravimetric Analysis (DSC/TGA) thermogram of crystalline Form D of Compound (I).

In some embodiments, crystalline Form D of Compound (I) is characterized as having one or more of:
a) an X-ray powder diffraction (XRPD) pattern substantially the same as shown in FIG. 7;
b) an X-ray powder diffraction (XRPD) pattern derived using Cu (Kα) radiation with peaks, in terms of 2-theta degrees, at about 8.2, 10.4, 12.1, 16.3, and 19.9±0.2 degrees;
c) unit cell parameters substantially equal to as shown in Table 27;
d) a Differential Scanning Calorimetry (DSC) thermogram substantially the same as shown in FIG. 9;
e) a Differential Scanning Calorimetry (DSC) thermogram with the endothermic events having an onset at about 93.0° C. and a peak at about 96.7° C.;
f) a Thermogravimetric Analysis (TGA) pattern substantially the same as shown in FIG. 9; g) a Thermogravimetric Analysis (TGA) pattern with an about 3.8% w/w loss from about 23.5° C. to about 85.0° C.; and an about 11.5% w/w loss from about 85.0° C. to about 120° C.; or h) combinations thereof.

Herein is also provided a crystalline form of Compound (I), characterized as Form D.

In one embodiment, the crystalline Form D of Compound (I), having an X-ray powder diffraction pattern derived using Cu (Kα) radiation comprising three, four, five or more peaks selected from the group consisting of: 8.2, 10.4, 12.1, 16.3, 19.9, and 21.0 (expressed in degrees 2-theta±0.2 degrees 2-theta).

In one embodiment, the crystalline Form D of Compound (I), having an X-ray powder diffraction pattern derived using Cu (Kα) radiation comprising one peak selected from the group consisting of: 8.2, 10.4, 12.1, 16.3, 19.9, and 21.0 (expressed in degrees 2-theta±0.2 degrees 2-theta).

In one embodiment, the crystalline Form D of Compound (I), having an X-ray powder diffraction pattern derived using Cu (Kα) radiation comprising two peaks selected from the group consisting of: 8.2, 10.4, 12.1, 16.3, 19.9, and 21.0 (expressed in degrees 2-theta±0.2 degrees 2-theta).

In one embodiment, the crystalline Form D of Compound (I), having an X-ray powder diffraction pattern derived using Cu (Kα) radiation comprising three peaks selected from the group consisting of: 8.2, 10.4, 12.1, 16.3, 19.9, and 21.0 (expressed in degrees 2-theta±0.2 degrees 2-theta).

In one embodiment, the crystalline Form D of Compound (I), having an X-ray powder diffraction pattern derived using Cu (Kα) radiation comprising four peaks selected from the group consisting of: 8.2, 10.4, 12.1, 16.3, 19.9, and 21.0 (expressed in degrees 2-theta±0.2 degrees 2-theta).

In one embodiment, the crystalline Form D of Compound (I), having an X-ray powder diffraction pattern derived using Cu (Kα) radiation comprising five or more peaks selected from the group consisting of: 8.2, 10.4, 12.1, 16.3, 19.9, and 21.0 (expressed in degrees 2-theta±0.2 degrees 2-theta).

Herein is also provided a crystalline Form D of Compound (I), having an X-ray powder diffraction pattern comprising a peak, in term of 2-theta degrees, at about 8.2 and about 16.3.

Herein is also provided a crystalline Form D of Compound (I), having the X-ray powder diffraction pattern comprises one or more 2-theta degrees selected from the group comprising about 8.2, 10.4, 12.1, 16.3, and 19.9 (each time plus or minus 0.2).

Herein is also provided a crystalline Form D of Compound (I), having unit cell parameters substantially equal to as shown in Table 27.

Figure 8:
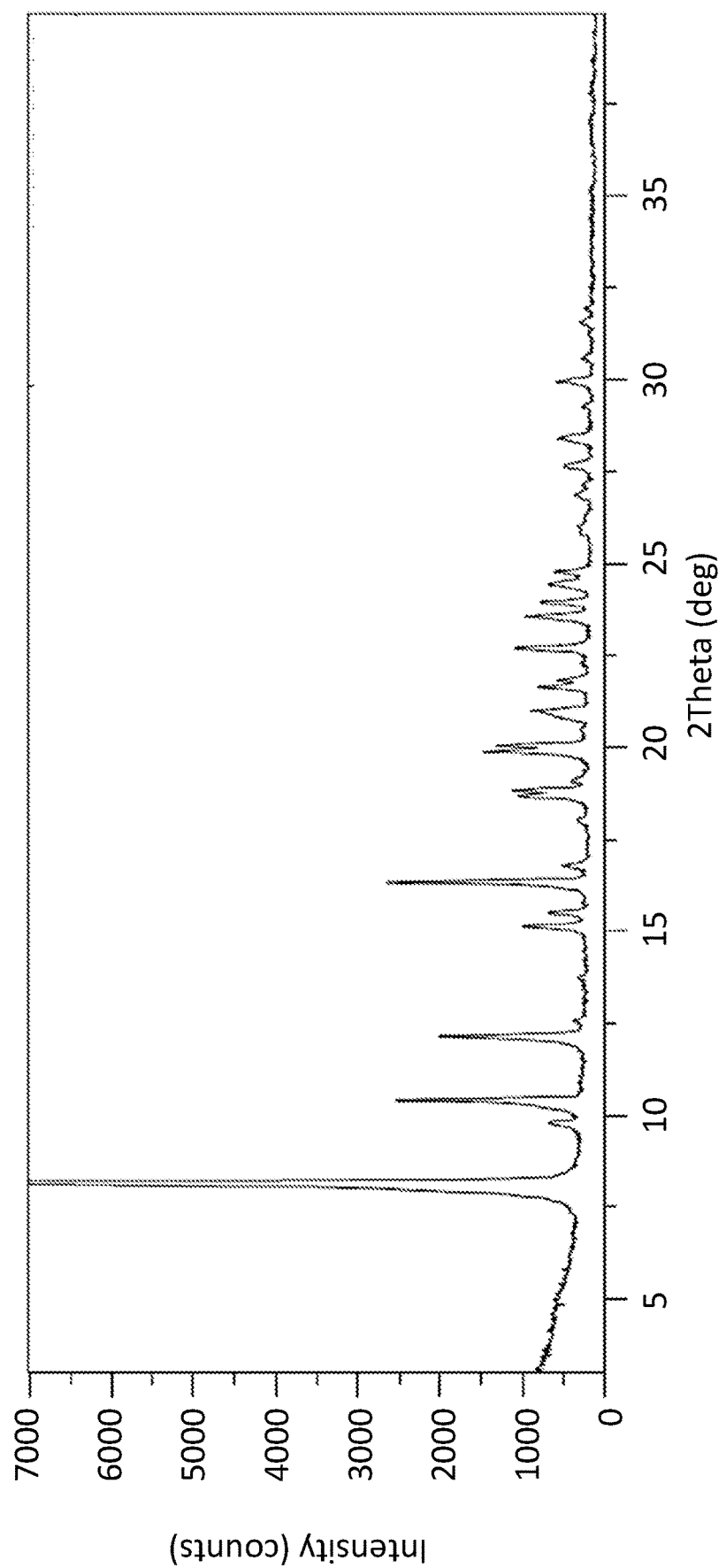
FIG. 8 is an X-ray powder diffractogram of crystalline Form D of Compound (I).

Herein is also provided a crystalline Form D of Compound (I), having the X-ray powder diffraction pattern is substantially in accordance with that shown in FIG. 8.

Herein is also provided a crystalline Form D of Compound (I), characterized by a differential scanning calorimetry (DSC) curve comprises an endotherm at about 93.0° C. and an endothermic peak at 96.7° C.

Herein are also provided processes for the preparation of the crystalline Form D of Compound (I) comprising at least the following steps:
  a) placing the crystalline Form C of Compound (I) in a first vial;
  b) placing the first vial into a second vial with isopropyl alcohol;
  c) sealing the second vial and keeping the second vial at room temperature for 10-16 days;
  d) isolating the solid to provide the crystalline Form D of Compound (I).

Herein is provided a crystalline Form E of Compound (I).

Figure 11:
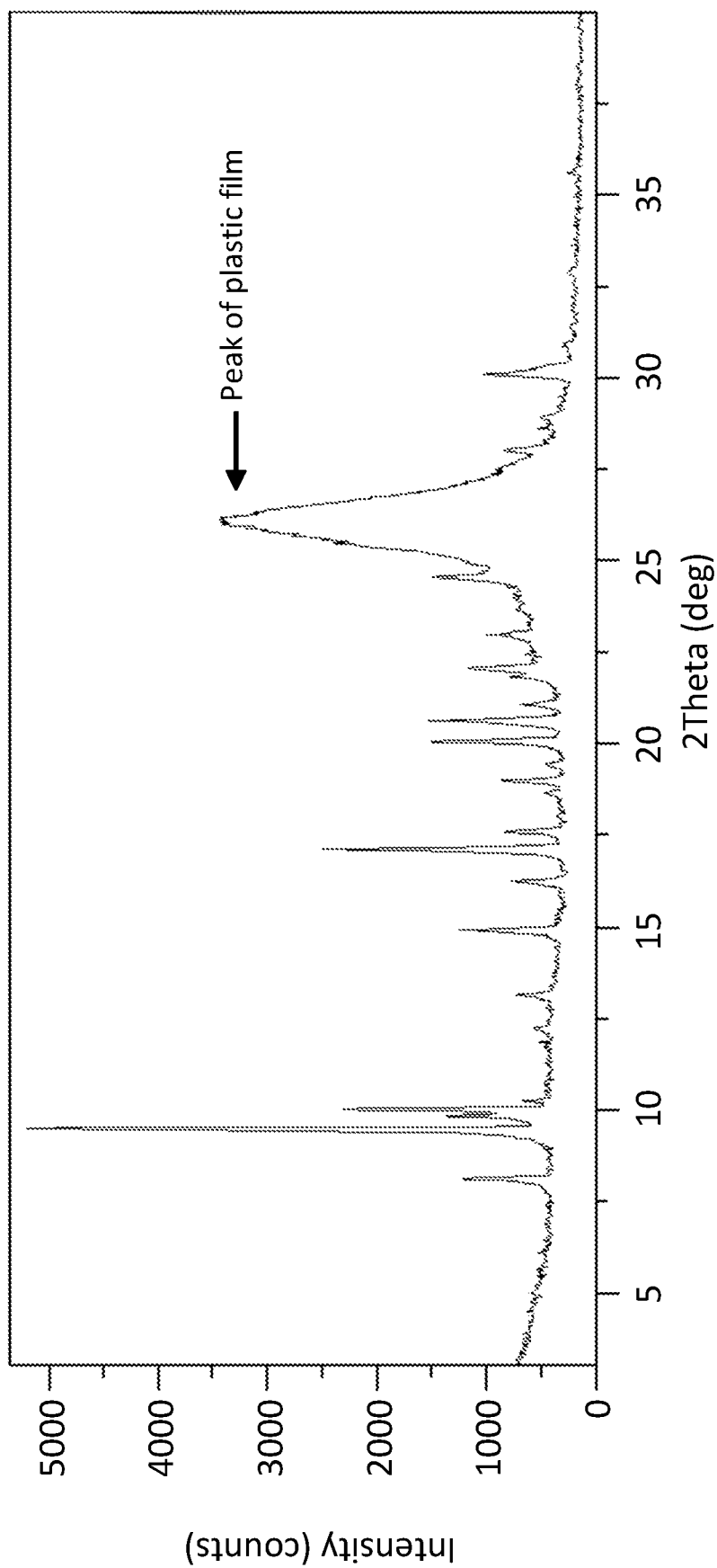
FIG. 11 is an X-ray powder diffractogram of crystalline Form E of Compound (I).

In some embodiments, crystalline Form E of Compound (I) is characterized as having one or more of:
  (a) an X-ray powder diffraction (XRPD) pattern substantially the same as shown in FIG. 11;
  (b) an X-ray powder diffraction (XRPD) pattern derived using Cu (Kα) radiation with peaks, in terms of 2-theta degrees, at about 9.5, 17.1, 20.1, 20.6, and 24.6±0.2 degrees.

Herein is also provided a crystalline form of Compound (I), characterized as Form E.

In one embodiment, the crystalline Form E of Compound (I), having an X-ray powder diffraction pattern derived using Cu (Kα) radiation comprising three, four, five, six or more peaks selected from the group consisting of: 8.11, 9.5, 10.0, 17.1, 20.1, 20.6, 24.6, and 30.1 (expressed in degrees 2-theta±0.2 degrees 2-theta).

In one embodiment, the crystalline Form E of Compound (I), having an X-ray powder diffraction pattern derived using Cu (Kα) radiation comprising one peak selected from the group consisting of: 8.11, 9.5, 10.0, 17.1, 20.1, 20.6, 24.6, and 30.1 (expressed in degrees 2-theta±0.2 degrees 2-theta).

In one embodiment, the crystalline Form E of Compound (I), having an X-ray powder diffraction pattern derived using Cu (Kα) radiation comprising two peaks selected from the group consisting of: 8.11, 9.5, 10.0, 17.1, 20.1, 20.6, 24.6, and 30.1 (expressed in degrees 2-theta±0.2 degrees 2-theta).

In one embodiment, the crystalline Form E of Compound (I), having an X-ray powder diffraction pattern derived using Cu (Kα) radiation comprising three peaks selected from the group consisting of: 8.11, 9.5, 10.0, 17.1, 20.1, 20.6, 24.6, and 30.1 (expressed in degrees 2-theta±0.2 degrees 2-theta).

In one embodiment, the crystalline Form E of Compound (I), having an X-ray powder diffraction pattern derived using Cu (Kα) radiation comprising four peaks selected from the group consisting of: 8.11, 9.5, 10.0, 17.1, 20.1, 20.6, 24.6, and 30.1 (expressed in degrees 2-theta±0.2 degrees 2-theta).

In one embodiment, the crystalline Form E of Compound (I), having an X-ray powder diffraction pattern derived using Cu (Kα) radiation comprising five peaks selected from the group consisting of: 8.11, 9.5, 10.0, 17.1, 20.1, 20.6, 24.6, and 30.1 (expressed in degrees 2-theta±0.2 degrees 2-theta).

In one embodiment, the crystalline Form E of Compound (I), having an X-ray powder diffraction pattern derived using Cu (Kα) radiation comprising six or more peaks selected from the group consisting of: 8.11, 9.5, 10.0, 17.1, 20.1, 20.6, 24.6, and 30.1 (expressed in degrees 2-theta±0.2 degrees 2-theta).

Herein is also provided a crystalline Form E of Compound (I) having the X-ray powder diffraction pattern is substantially in accordance with that shown in FIG. 9.

Herein is also provided a crystalline Form E of Compound (I), having an X-ray powder diffraction pattern comprising a peak, in term of 2-theta degree, at about 9.5, 17.1, 20.1, 20.6, and 24.6±0.2 degrees.

Herein are also provided processes for the preparation of the crystalline Form E of Compound (I) comprising at least the following steps:
  a) dissolving Compound (I) in dichloromethane to give a suspension;
  b) filtering the suspension to give a filtrate;
  c) placing the filtrate in a vial and covering with a film;
  d) evaporating at room temperature to give the crystalline Form E of Compound (I).

Figure 12:
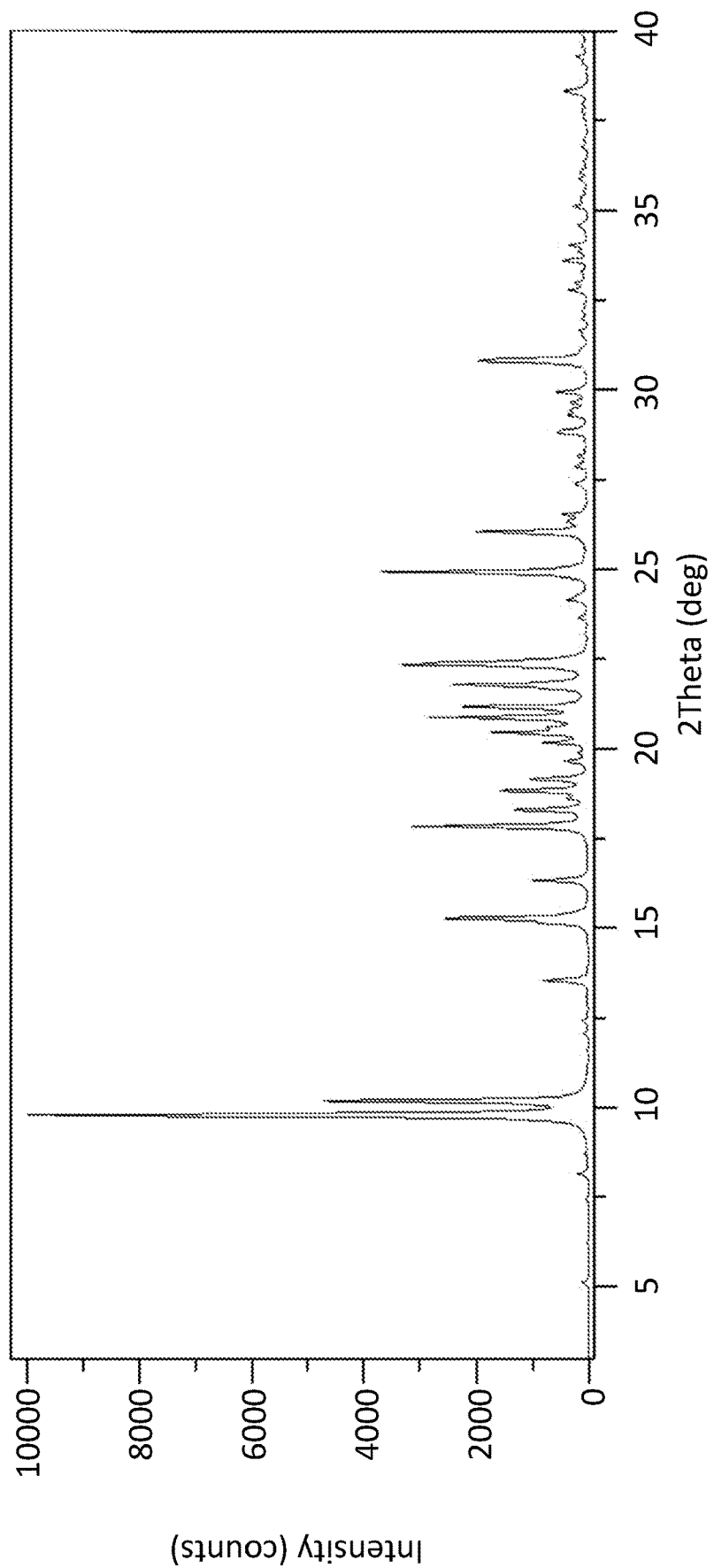
FIG. 12 is an X-ray powder diffractogram of crystalline Form F of Compound (I).

In one aspect, provided herein is crystalline Form F of Compound (I). In some embodiments, crystalline Form F of Compound (I) is characterized as having one or more of:
  (a) an X-ray powder diffraction (XRPD) pattern substantially the same as shown in FIG. 12;
  (b) an X-ray powder diffraction (XRPD) pattern derived using Cu (Kα) radiation with peaks, in terms of 2-theta degrees, at about 9.8, 10.2, 17.8, 22.3, and 24.9±0.2 degrees.

Herein is also provided a crystalline form of Compound (I), characterized as Form F.

In one embodiment, the crystalline Form F of Compound (I), having an X-ray powder diffraction pattern derived using Cu (Kα) radiation comprising three, four, five, six or more peaks selected from the group consisting of: 9.8, 10.2, 17.8, 20.9, 21.1, 21.8, 22.3, and 24.9 (expressed in degrees 2-theta±0.2 degrees 2-theta).

In one embodiment, the crystalline Form F of Compound (I), having an X-ray powder diffraction pattern derived using Cu (Kα) radiation comprising one peak selected from the group consisting of: 9.8, 10.2, 17.8, 20.9, 21.1, 21.8, 22.3, and 24.9 (expressed in degrees 2-theta±0.2 degrees 2-theta).

In one embodiment, the crystalline Form F of Compound (I), having an X-ray powder diffraction pattern derived using Cu (Kα) radiation comprising two peaks selected from the group consisting of: 9.8, 10.2, 17.8, 20.9, 21.1, 21.8, 22.3, and 24.9 (expressed in degrees 2-theta±0.2 degrees 2-theta).

In one embodiment, the crystalline Form F of Compound (I), having an X-ray powder diffraction pattern derived using Cu (Kα) radiation comprising three peaks selected from the group consisting of: 9.8, 10.2, 17.8, 20.9, 21.1, 21.8, 22.3, and 24.9 (expressed in degrees 2-theta±0.2 degrees 2-theta).

In one embodiment, the crystalline Form F of Compound (I), having an X-ray powder diffraction pattern derived using Cu (Kα) radiation comprising four peaks selected from the group consisting of: 9.8, 10.2, 17.8, 20.9, 21.1, 21.8, 22.3, and 24.9 (expressed in degrees 2-theta±0.2 degrees 2-theta).

In one embodiment, the crystalline Form F of Compound (I), having an X-ray powder diffraction pattern derived using Cu (Kα) radiation comprising five peaks selected from the group consisting of: 9.8, 10.2, 17.8, 20.9, 21.1, 21.8, 22.3, and 24.9 (expressed in degrees 2-theta±0.2 degrees 2-theta).

In one embodiment, the crystalline Form F of Compound (I), having an X-ray powder diffraction pattern derived using Cu (Kα) radiation comprising six or more peaks selected from the group consisting of: 9.8, 10.2, 17.8, 20.9, 21.1, 21.8, 22.3, and 24.9 (expressed in degrees 2-theta±0.2 degrees 2-theta).

Figure 10:
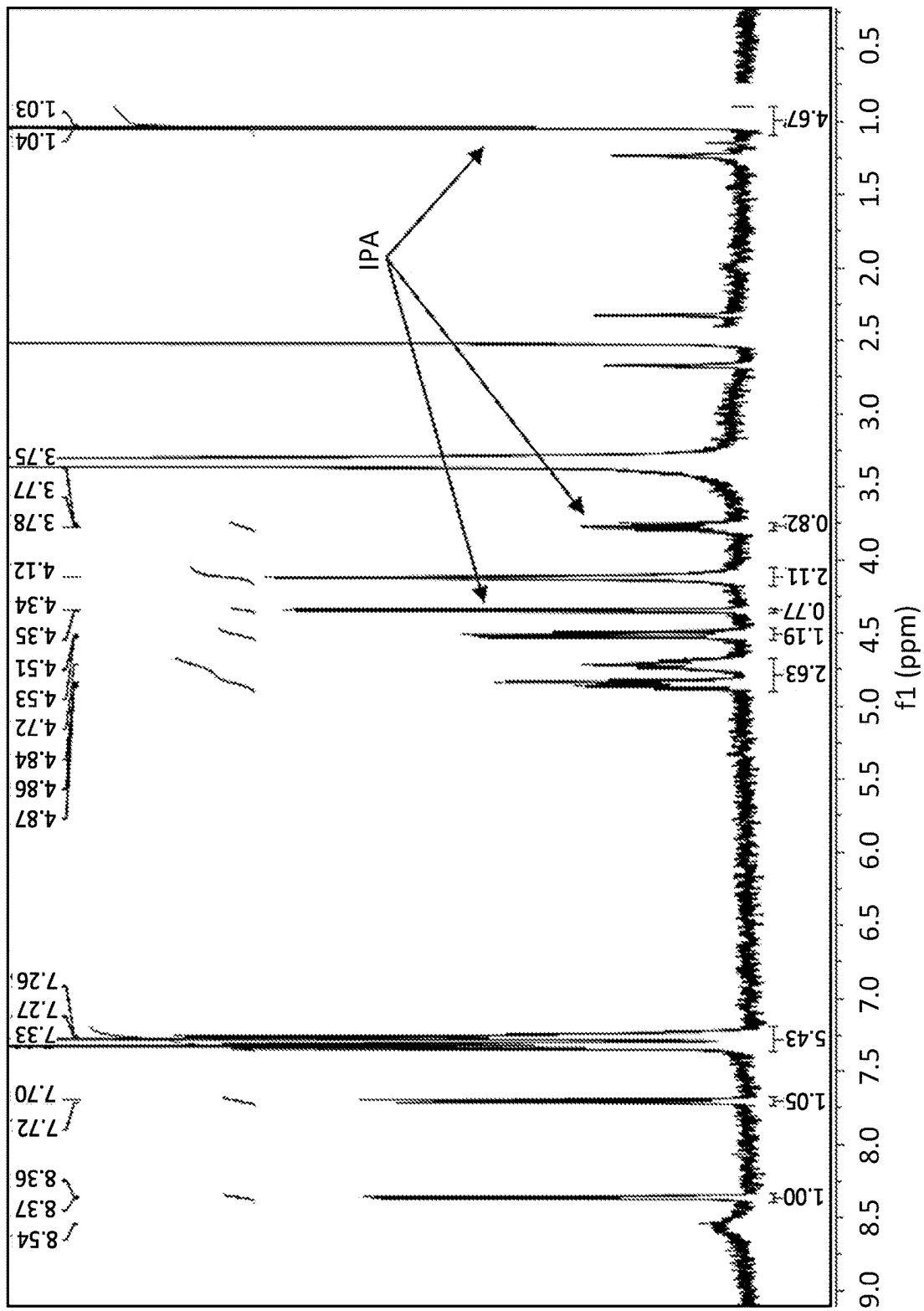
FIG. 10 is a $^1$HNMR spectrum of crystalline Form D of Compound (I).

Herein is also provided a crystalline Form F of Compound (I), having the X-ray powder diffraction pattern is substantially in accordance with that shown in FIG. 10.

Herein is also provided a crystalline Form F of Compound (I), having an X-ray powder diffraction pattern comprising a peak, in term of 2-theta degree, at about 9.8, 10.2, 17.8, 22.3, and 24.9 (expressed in degrees 2-theta±0.2 degrees 2-theta).

Herein are also provided processes for the preparation of the crystalline Form F of Compound (I) comprising at least the following steps:
a) dissolving Compound (I) in a solvent selected from MeOH and MeOH/H$_2$O to form a slurry;
b) stirring the slurry at a set temperature ranging from 40° C. to 60° C.;
c) slowly cooling down to 1-10° C.;
d) filtering, washing with the solvent and drying to provide the crystalline Form F of Compound (I).

Preparation of Compound (I)

The compounds described herein may be made from commercially available starting materials or synthesized using known organic, inorganic, and/or enzymatic processes. By way of example, the Compound (I) can be synthesized using the methods described in WO 2017/136727 (also see U.S. Pat. No. 9,815,850), together with synthetic methods known in the art of synthetic organic chemistry, or variations thereon as appreciated by those skilled in the art.

Pharmaceutical Compositions

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the compounds described herein are administered either alone or in combination with pharmaceutically acceptable excipients, in a pharmaceutical composition. Administration of the compounds and compositions described herein can be affected by any method that enables delivery of the compounds to the site of action.

In some embodiments, pharmaceutical compositions suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent.

In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

It should be understood that in addition to the ingredients particularly mentioned above, the compounds and compositions described herein may include other agents conventional in the art having regard to the type of formulation in question, for example those suitable for oral administration may include flavoring agents.

Herein is also provided a pharmaceutical composition comprising a crystalline Form A of Compound (I) and a pharmaceutically acceptable excipient. In one aspect, in said pharmaceutical composition, said crystalline Form A is substantially pure and substantially free of other crystalline forms of Compound (I). In another aspect, in said pharmaceutical composition, said crystalline Form A is at least 90 percent by weight of all forms.

Herein is also provided a pharmaceutical composition comprising a crystalline Form B of Compound (I) and a pharmaceutically acceptable excipient. In one aspect, in said pharmaceutical composition, said crystalline Form B is substantially pure and substantially free of alternative forms. In another aspect, in said pharmaceutical composition, said crystalline Form B is at least 90 percent by weight of all forms.

Herein is also provided a pharmaceutical composition comprising a crystalline Form C of Compound (I) and a pharmaceutically acceptable excipient. In one aspect, in said pharmaceutical composition, said crystalline Form C is substantially pure and substantially free of alternative forms. In another aspect, in said pharmaceutical composition, said crystalline Form C is at least 90 percent by weight of all forms.

Herein is also provided a pharmaceutical composition comprising a crystalline Form D of Compound (I) and a pharmaceutically acceptable excipient. In one aspect, in said pharmaceutical composition, said crystalline Form D is substantially pure and substantially free of alternative forms. In another aspect, in said pharmaceutical composition, said crystalline Form D is at least 90 percent by weight of all forms.

Herein is also provided a pharmaceutical composition comprising a crystalline Form E of Compound (I) and a pharmaceutically acceptable excipient. In one aspect, in said pharmaceutical composition, said crystalline Form E is substantially pure and substantially free of alternative forms. In another aspect, in said pharmaceutical composition, said crystalline Form E is at least 90 percent by weight of all forms.

Herein is also provided a pharmaceutical composition comprising a crystalline Form F of Compound (I) and a pharmaceutically acceptable excipient. In one aspect, in said pharmaceutical composition, said crystalline Form F is substantially pure and substantially free of alternative forms. In another aspect, in said pharmaceutical composition, said crystalline form F is at least 90 percent by weight of all forms.

Methods of Dosing and Treatment Regimens

The daily dosage may be described as a total amount of a compound disclosed herein administered per dose or per day. Daily dosage of a compound disclosed herein may be between about 1 mg and 4,000 mg, between about 1 to 2,000 mg/day, between about 1 to 1,000 mg/day, between about 10 to 500 mg/day, between about 20 to 500 mg/day, between about 50 to 300 mg/day, between about 75 to 200 mg/day, or between about 15 to 150 mg/day.

When administered orally, the total daily dosage for a human patient may be between 1 mg and 1,000 mg, between about 1,000-2,000 mg/day, between about 10-500 mg/day, between about 50-300 mg/day, between about 75-200 mg/day, or between about 100-150 mg/day.

In certain embodiments, the method comprises administering to the patient an initial daily dose of about 1 to 800 mg of a compound described herein and increasing the dose by increments until clinical efficacy is achieved. Increments of about 5, 10, 25, 50, or 100 mg can be used to increase the dose. The dosage can be increased daily, every other day, twice per week, or once per week.

Herein is also provided a method of treating a disease or disorder mediated by RIPK1 in a patient in need thereof, comprising administering to the patient an effective amount of the crystalline Form A of Compound (I).

Herein is also provided the crystalline Form A of Compound (I) for use as a medicine, for use as an inhibitor RIPK1 receptor, and for use in the treatment of various diseases wherein RIPK1 receptor is involved.

Herein is also provided use of the crystalline Form A of Compound (I) for the manufacture of a medicament for treating a disease involving inhibition of RIPK1 receptor.

Herein is also provided a method of treating a disease or disorder mediated by RIPK1 in a patient in need thereof, comprising administering to the patient an effective amount of the crystalline Form B of Compound (I).

Herein is also provided the crystalline Form B of Compound (I) for use as a medicine, for use as an inhibitor RIPK1 receptor, and for use in the treatment of various diseases wherein RIPK1 receptor is involved.

Herein is also provided use of the crystalline Form B of Compound (I) for the manufacture of a medicament for treating a disease involving inhibition of RIPK1 receptor.

Herein is also provided a method of treating a disease or disorder mediated by RIPK1 in a patient in need thereof, comprising administering to the patient an effective amount of the crystalline Form C of Compound (I).

Herein is also provided the crystalline Form C of Compound (I) for use as a medicine, for use as an inhibitor RIPK1 receptor, and for use in the treatment of various diseases wherein RIPK1 receptor is involved.

Herein is also provided use of the crystalline Form C of Compound (I) for the manufacture of a medicament for treating a disease involving inhibition of RIPK1 receptor.

Herein is also provided a method of treating a disease or disorder mediated by RIPK1 in a patient in need thereof, comprising administering to the patient an effective amount of the crystalline Form D of Compound (I).

Herein is also provided the crystalline Form D of Compound (I) for use as a medicine, for use as an inhibitor RIPK1 receptor, and for use in the treatment of various diseases wherein RIPK1 receptor is involved.

Herein is also provided use of the crystalline Form D of Compound (I) for the manufacture of a medicament for treating a disease involving inhibition of RIPK1 receptor.

Herein is also provided a method of treating a disease or disorder mediated by RIPK1 in a patient in need thereof, comprising administering to the patient an effective amount of the crystalline Form E of Compound (I).

Herein is also provided the crystalline Form E of Compound (I) for use as a medicine, for use as an inhibitor RIPK1 receptor, and for use in the treatment of various diseases wherein RIPK1 receptor is involved.

Herein is also provided use of the crystalline Form E of Compound (I) for the manufacture of a medicament for treating a disease involving inhibition of RIPK1 receptor.

Herein is also provided a method of treating a disease or disorder mediated by RIPK1 in a patient in need thereof, comprising administering to the patient an effective amount of the crystalline form F of Compound (I).

Herein is also provided the crystalline Form F of Compound (I) for use as a medicine, for use as an inhibitor RIPK1 receptor, and for use in the treatment of various diseases wherein RIPK1 receptor is involved.

Herein is also provided use of the crystalline Form F of Compound (I) for the manufacture of a medicament for treating a disease involving inhibition of RIPK1 receptor.

Articles of Manufacture and Kits

Disclosed herein, in certain embodiments, are kits and articles of manufacture for use with one or more methods described herein. In some embodiments, additional component of the kit comprises a package or container that is compartmentalized to receive one or more containers such as vials, tubes, and the like, each of the container(s) comprising one of the separate elements to be used in a method described herein. Suitable containers include, for example, bottles, vials, plates, syringes, and test tubes. In one embodiment, the containers are formed from a variety of materials such as glass or plastic.

The articles of manufacture provided herein contain packaging materials. Examples of pharmaceutical packaging materials include, but are not limited to, bottles, tubes, bags, containers, and any packaging material suitable for a selected formulation and intended mode of use.

For example, the container(s) include one or more of the compounds described herein. Such kits optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself, a label is associated with a container when it is present within a receptacle or excipient that also holds the container, e.g., as a package insert. In one embodiment, a label is used to indicate that the contents are to be used for a specific therapeutic application. The label also indicates directions for use of the contents, such as in the methods described herein.

Abbreviations

ACN or MeCN: acetonitrile;
CAN: ceric ammonium nitrate;
CPME: cyclopentyl methyl ether;
DCM: dichloromethane;
DMSO: dimethylsulfoxide;
DMAc: N,N-Dimethylacetamide;
DSC: differential scanning calorimetry;
DVS: dynamic vapor sorption;
Et: ethyl;
EtOAc: ethyl acetate;
EtOH: ethanol;
equiv or eq.: equivalents;
FaSSIF: fasted state simulated intestinal fluid;
FeSSIF: fed state simulated intestinal fluid;
FTIR: Fourier transform infrared;
h or hr: hour;
hrs: hours;
HPLC: high-performance liquid chromatography;
IPA: isopropyl alcohol;
IPAc: isopropyl acetate;
KCl: potassium chloride;
LC-MS or LCMS or LC/MS: liquid chromatography-mass spectrometry;
LiCl: lithium chloride;
M: molar;
Me: methyl;
MeOH: methanol;
MeOAc: methyl acetate;
$Mg(NO_3)_2$: magnesium nitrate;
MIBK: methyl isobutyl ketone;
MTBE: methyl tert-butyl ether;
mins or min: minutes;
$N_2$: nitrogen;
n-PrOAc: n-propyl acetate;
NMR: nuclear magnetic resonance;
RH: relative humidity;
rt or RT: room temperature;
SCXRD: single crystal x-ray diffraction;
SGF: simulated gastric fluid;
TFA: trifluoroacetic acid;
TGA: thermogravimetic analysis;
THF: tetrahydrofuran;
2-MeTHF: 2-methyltetrahydrofuran;
vol: volume;
w/w: weight ratio; and
XRPD: X-ray powder diffraction.

The following examples are provided for illustrative purposes only and not to limit the scope of the claims provided herein.

Instruments and Methods

1. XRPD

For XRPD analysis, PANalytical Empyrean and X' Pert3 X-ray powder diffractometer were used. The XRPD parameters used are listed in Table 1.

TABLE 1

Parameters for XRPD test

| Parameters | Empyrean | X' Pert3 | X' Pert3 |
|---|---|---|---|
| X-Ray wavelength | Cu, Kα; Kα1 (Å): 1.540598 Kα2 (Å): 1.544426 intensity ratio Kα2/Kα1: 0.50 | Cu, Kα; Kα1 (Å): 1.540598 Kα2 (Å): 1.544426 intensity ratio Kα2/Kα1: 0.50 | Cu, Kα; Kα1 (Å): 1.540598 Kα2 (Å): 1.544426 intensity ratio Kα2/Kα1: 0.50 |
| X-Ray tube setting | 45 kV, 40 mA | 45 kV, 40 mA | 45 kV, 40 mA |
| Divergence slit | Automatic | ⅛° | ⅛° |
| Scan mode | Continuous | Continuous | Continuous |
| Scan range (2θ/°) | 3°~40° | 3°~40° | 3°~40° |
| Step size (2θ/°) | 0.0167° | 0.0263° | 0.0263° |
| Scan step time (s) | 17.780 | 46.665 | 39.525 |
| Test time (s) | About 5 mins 30 s | About 5 mins | About 4-6 mins |

2. TGA and DSC

TGA data were collected using a TA Q500/Q5000 TGA from TA Instruments. DSC was performed using a TA Q200/Q2000 DSC from TA Instruments. Detailed parameters used are listed in Table 2.

TABLE 2

Parameters for TGA and DSC test

| Parameters | TGA | DSC |
|---|---|---|
| Method | Ramp | Ramp |
| Sample pan | Aluminum, open | Aluminum, crimped/open |
| Temperature | RT- desired temperature | 25° C. - desired temperature |
| Heating rate | 10° C./min | 10° C./min |
| Purge gas | $N_2$ | $N_2$ |

3. DVS

DVS was measured via a SMS (Surface Measurement Systems) DVS Intrinsic. The relative humidity at 25° C. were calibrated against deliquescence point of LiCl, $Mg(NO_3)_2$ and KCl. Parameters for DVS test were listed in Table 3.

TABLE 3

Parameters for DVS test

| Parameters | DVS |
|---|---|
| Temperature | 25° C. |
| Sample size | 10~20 mg |

TABLE 3-continued

Parameters for DVS test

| Parameters | DVS |
| --- | --- |
| Gas and flow rate | N₂, 200 mL/min |
| dm/dt | 0.002%/min |
| Min. dm/dtstabilityduration | 10 min |
| Max. equilibrium time | 180 min |
| RH range | 95% RH-0% RH-95% RH |
| RH step size | 10% (90% RH-0% RH-90% RH) |
| | 5% (95% RH-90% RH and 90% RH-95% RH) |

4. ¹H Solution NMR

¹H Solution NMR was collected on Bruker 400M NMR Spectrometer using DMSO-d6.

1. HPLC

Agilent HPLC was utilized and detailed chromatographic conditions for purity and solubility measurement are listed in Table 4.

TABLE 4

Chromatographic conditions and parameters for purity/solubility test

| Parameters | Agilent 1260 DAD Detector | |
| --- | --- | --- |
| Column | Halo C18 100 × 4.6 mm, 2.7 μm | |
| Mobile phase | A: 0.05% TFA in H₂O | |
| | B: 0.05% TFA in ACN | |
| | Time (min) | % B |
| Gradient table | 0.0 | 10 |
| | 12.0 | 95 |
| | 15.0 | 95 |
| | 20.0 | 10 |
| Run time | 20.0 min | |
| Post time | 0.0 min | |
| Flow rate | 1.0 mL/min | |
| Injection volume | 5 μL | |
| Detector wavelength | UV at 220 nm | |
| Column temperature | 40° C. | |
| Sampler temperature | RT | |
| Diluent | ACN:H₂O = 1:1 (v:v) | |

2. SCXRD

The single crystal X-ray diffraction data was collected at 175K using Bruker D8 VENTURE diffractometer (Mo/Kα radiation, μ=0.71073 Å). The microscopic picture was captured using Shanghai Cewei stereo microscope. The experimental XRPD of the single crystal sample and reference of Compound (I) Form B were collected by PANalytical X'Pert powder diffractometer. The instrument parameters were shown in Table 5.

TABLE 5

SCXRD instrument parameters

| Instrument | Bruke D8 Venture |
| --- | --- |
| X-Ray sources generator | TXS Microfocus Rotating Anode X-ray Source |
| | (Mo/Kα: 0.71073 Å) |
| | Focus spot: 100 μm; Power: 2.5 kW |
| Detector | PHOTON 100 CMOS detector |
| | (Active area: 100 × 100 mm²) |

TABLE 5-continued

SCXRD instrument parameters

| Instrument | Bruke D8 Venture |
| --- | --- |
| Goniometer | FIXED-CHI Goniometer |
| Low Temperature Devices | Cobra (Oxford Cryosystems) |
| Software package | APEX3 |

EXAMPLES

Example 1: Preparation of Form a of Compound (I)

To 100 mg of Compound (I) was added 0.9 mL toluene, 0.1 mL methylcyclohexane. The mixture was heated to 60° C. and the solid dissolved to give a homogeneous solution. The solution was cooled down and a gummy precipitation was observed. The mixture was left for 3 days with stirring and the precipitated material remained a gum. A few drops of diisopropyl ether were added at room temperature. The mixture was then heated to 60° C. and a small amount of what appeared to be powdery solid residue remained undissolved. When allowed to cool a lot of precipitation occurred but the precipitated solids appeared to be part powder/part gum. This mixture was heated to 60° C. again and kept at this temperature for 6 hours—more powdery solid precipitated directly when hot. The mixture was allowed to cool and stirred at room temperature overnight then filtered and washed with toluene (1 mL) to give about 77 mg of white solid.

As displayed in FIG. 1, XRPD revealed that Example 1 is crystalline and thus named as Form A. The crystalline form A can therefore be characterized by having one or more X-ray powder diffraction displaying peaks expressed as 2-theta degrees at about 6.9, 13.0, 16.6 and 23.4 (each time plus or minus 0.2), which optionally further shows one or more of the following peaks expressed as 2-theta degrees at: about 13.9, 19.4, 11.5, and 24.0 (each time plus or minus 0.2), or optionally further characterized by a powder X-ray diffractogram as substantially illustrated in FIG. 1. A characteristic X-ray powder diffractogram of the crystalline Form A of Compound (I) can be given substantially in FIG. 1 and its characteristic signals are summarized in the following Table 6.

TGA and DSC data of Example 1 are shown in FIG. 2. A weight loss of 1.0% was observed up to 150° C. on the TGA curve. The DSC result exhibited an endothermic onset at 186.7° C. (plus or minus 2 degrees C.) and an endothermic peak at 188.9° C. (plus or minus 2 degrees C.). As indicated in the FIG. 2, this melting point temperature is associated with a high enthalpy of fusion ΔHf (nearly 91.7 J/g). According to the results, Form A is characterized to be an anhydrate.

TABLE 6

XRPD Peak list of Form A

| Pos. [°2Th.] (±0.2) | d-spacing [Å] | Rel. Int. [%] |
| --- | --- | --- |
| 6.9 | 12.82 | 100.00 |
| 11.5 | 7.71 | 56.15 |
| 13.0 | 6.83 | 18.2 |
| 13.9 | 6.38 | 86.83 |
| 15.5 | 5.70 | 4.28 |
| 16.6 | 5.34 | 86.54 |

TABLE 6-continued

XRPD Peak list of Form A

| Pos. [°2Th.] (±0.2) | d-spacing [Å] | Rel. Int. [%] |
|---|---|---|
| 17.8 | 5.00 | 22.35 |
| 18.3 | 4.84 | 7.64 |
| 19.0 | 4.67 | 15.82 |
| 19.4 | 4.58 | 63.79 |
| 19.9 | 4.46 | 33.01 |
| 20.3 | 4.37 | 10.32 |
| 21.0 | 4.23 | 31.03 |
| 21.3 | 4.18 | 16.27 |
| 21.8 | 4.08 | 12.69 |
| 22.3 | 3.98 | 18.47 |
| 23.4 | 3.81 | 86.54 |
| 24.0 | 3.71 | 65.04 |
| 26.2 | 3.40 | 33.80 |
| 26.9 | 3.31 | 7.82 |
| 27.3 | 3.26 | 13.21 |
| 28.0 | 3.18 | 15.87 |
| 29.3 | 3.05 | 10.06 |
| 29.9 | 2.99 | 5.60 |
| 35.2 | 2.55 | 11.32 |
| 36.1 | 2.49 | 5.52 |

Examples 2: Preparation of Solid-State Forms by Slurry at 50° C. Method

Slurry conversion experiments were also conducted at 50° C. in 12 different solvent systems. About 15 mg of starting material (Example 1) was suspended in 0.5 mL of solvent in an HPLC vial. After the suspension was magnetically stirred (~1000 rpm) for about 2 days at 50° C., the remaining solids were isolated for XRPD analysis. Slurry conversion experiments results were summarized in Table 7.

TABLE 7

Summary of slurry conversion experiments at 50° C.

| Example | Solvent (v/v) | Solid Form |
|---|---|---|
| 2-1 | IPAc | Form B |
| 2-2 | EtOH | Form B |
| 2-3 | IPA | Form A + B |
| 2-4 | MIBK | Form B |
| 2-5 | EtOAc | Form B |
| 2-6 | CPME | Form A |
| 2-7 | Toluene | Form A |
| 2-8 | H$_2$O | Form B |
| 2-9 | MeOH/IPAc (1:4) | Form B |
| 2-10 | EtOH/MeOAc (1:4) | Form B |
| 2-11 | NMP/Toluene (1:4) | Form A |
| 2-12 | THF/H$_2$O (1:4) | Form B |

As displayed in FIG. 3, XRPD revealed that Example 2-1 is crystalline and thus named as Form B. The crystalline Form B can be characterized by having the X-ray powder diffraction displaying one or more peaks expressed as 2-Theta degree at about 9.6, 11.5, 16.4, 19.2, 23.2 and 23.8 (each time plus or minus 0.2), which optionally further shows the following peaks expressed as 2-Theta degrees at: about 13.8 (each time plus or minus 0.2), optionally further characterized by a powder X-ray diffractogram as substantially illustrated in FIG. 3 and its characteristic signals are summarized in the following Table 8.

TGA and DSC data of Example 2-1 are shown in FIG. 4. A weight loss of 1.0% was observed up to 150° C. on the TGA curve. The DSC result exhibited an endothermic onset at 189.2° C. (plus or minus 2 degrees C.) and an endothermic peak at 191.9° C. (plus or minus 2 degrees C.). As indicated in the FIG. 4, this melting point temperature is associated with a high enthalpy of fusion AHf (nearly 93.4 J/g). According to the results, Form B is characterized to be an anhydrate. XRPD of Example 2-2, 2-4, 2-5, 2-8, 2-9, 2-10 and 2-12 is consistent with FIG. 3.

TABLE 8

XRPD Peak list of Form B (Example 2-1)

| Pos. [°2Th.] (±0.2) | d-spacing [Å] | Rel. Int. [%] |
|---|---|---|
| 9.6 | 9.26 | 100.00 |
| 11.5 | 7.71 | 31.94 |
| 13.8 | 6.42 | 38.58 |
| 15.3 | 5.79 | 6.40 |
| 16.4 | 5.41 | 74.52 |
| 17.8 | 4.99 | 4.88 |
| 19.2 | 4.63 | 61.05 |
| 21.7 | 4.10 | 10.42 |
| 23.2 | 3.84 | 54.87 |
| 23.8 | 3.74 | 42.05 |
| 24.6 | 3.61 | 17.53 |
| 25.9 | 3.44 | 12.52 |
| 27.9 | 3.20 | 18.27 |
| 29.4 | 3.03 | 5.02 |
| 33.1 | 2.71 | 1.40 |
| 37.4 | 2.41 | 6.51 |

Examples 3: Preparation of Solid-State Forms by Slurry Cycling (50-5° C.) Method Slurry cycling (50-5° C.) experiments were conducted in 6 different solvent systems. About 15 mg of starting material (Example 1) was suspended in 0.5 mL of solvent in an HPLC vial. The suspensions were magnetically stirred (~600 rpm) at 50° C. for 1 hr and then slowly cooled down to 5° C. at a rate of 0.1° C./min. The obtained solids were kept isothermal at 5° C. after cycled between 50° C. and 5° C. for 3 times. Solids were isolated for XRPD analysis. XPRD of Example 3-1, 3-2, 3-3, 3-6 are consistent with FIG. 3, so they are also Form B. Results summarized in Table 9 indicate that Form A, B and A+B were generated.

TABLE 9

Summary of slurry cycling (50-5° C.) experiments

| Example | Solvent (v/v) | Solid Form |
|---|---|---|
| 3-1 | MIBK | Form B |
| 3-2 | IPAc | Form B |
| 3-3 | H$_2$O | Form B |
| 3-4 | n-PrOAc | Form A + B |
| 3-5 | CPME | Form A |
| 3-6 | dimethyl carbonate | Form B |

Examples 4: Preparation of Solid-State Forms by Slow Cooling Method

Slow cooling experiments were conducted in 10 solvent systems. About 15 mg of starting material (Example 1) was suspended in 1.0 mL of solvent in an HPLC vial at RT. The suspension was then heated to 50° C., equilibrated for about 2 hrs and filtered to a new vial using a PTFE membrane (pore size of 0.45 m) to remove undissolved material. Filtrate was slowly cooled down to 5° C. at a rate of 0.1° C./min. The obtained solids were kept isothermal at 5° C. before isolated for XRPD analysis. Clear solutions were evaporated to dryness at RT and then solids were tested by XRPD. XPRD of Example 4-10 is consistent with FIG. 3, so it is also Form B. Results summarized in Table 10 indicated Form A, Form B and amorphous material were obtained.

TABLE 10

Summary of slow cooling experiments

| Example | Solvent (v/v) | Solid Form |
|---|---|---|
| 4-1 | EtOH | Form A |
| 4-2 | IPA | Form A |
| 4-3 | Acetone | Form A |
| 4-4 | MIBK | Form A |
| 4-5 | EtOAc | Form A |
| 4-6* | IPAc | Form A |
| 4-7* | THF | Amorphous |
| 4-8 | ACN | Form A |
| 4-9* | MeOH/IPAc (1:1) | Amorphous |
| 4-10 | DMAc/H$_2$O (1:4) | Form B |

*Clear solution obtained after cooling and the solid was obtained via evaporation at RT.

Examples 5: Preparation of Solid-State Forms by Slurry at RT Method

Slurry conversion experiments were conducted at RT in 14 different solvent systems. Around 15 mg of starting material (Example 1) was suspended in 0.5 mL of solvent in an HPLC vial. After the suspension was stirred magnetically (~1000 rpm) for about 13 days at RT, the remaining solids were isolated for XRPD analysis. Results summarized in Table 11 indicated that Form A and B were generated.

TABLE 11

Summary of slurry conversion experiments at RT

| Example | Solvent (v/v) | Solid Form |
|---|---|---|
| 5-1 | EtOH | Form B |
| 5-2* | IPA | Form B |
| 5-3* | MIBK | Form B |
| 5-4 | EtOAc | Form B |
| 5-5 | MTBE | Form A |
| 5-6 | dimethyl carbonate | Form B |
| 5-7* | n-PrOAc | Form B |
| 5-8 | H$_2$O | Form B |
| 5-9* | IPA/H$_2$O (0.97:0.03, aw~0.3) | Form B |
| 5-10* | IPA/H$_2$O (0.92:0.08, aw~0.6) | Form B |
| 5-11* | IPA/H$_2$O (0.77:0.23, aw~0.9) | Form B |
| 5-12 | EtOH/IPAc (1:1) | Form B |
| 5-13 | THF/n-Heptane (1:4) | Form A |
| 5-14 | MeOH/Toluene (1:4) | Form B |

*The XRPD results showed the samples were Form A after stirring for 2 days, while their forms turned to Form B after stirring for about 13 days.

Examples 6: Preparation of Solid-State Forms by Vapor-Solid Diffusion Method

Vapor-solid diffusion experiments were performed using 10 different solvents. About 15 mg of sample (Example 1) was weighed into a 3-mL glass vial. This 3-mL vial was then placed into a 20-mL vial with 4 mL of solvents. The 20-mL vial was sealed with a cap and kept at RT for 13~14 days. The solids were isolated for XRPD analysis. The results summarized in Table 12 showed that Form A, B and A+B were observed.

TABLE 12

Summary of vapor-solid diffusion experiments

| Example | Solvent | Solid Form |
|---|---|---|
| 6-1 | MeOH | Form B |
| 6-2 | Acetone | Form A |
| 6-3 | THF | Form A + B |
| 6-4 | ACN | Form A |
| 6-5 | EtOH | Form A |
| 6-6 | IPA | Form A |
| 6-7 | EtOAc | Form A |
| 6-8 | MeOAc | Form A |
| 6-9 | 2-MeTHF | Form A |
| 6-10 | DMSO | Form A + B |

Examples 7: Preparation of Solid-State Forms by Vapor-Solution Diffusion Method

Vapor-solution diffusion experiments were conducted in 8 different solvents. Approximate 15 mg of starting material (Example 1) was dissolved in 0.2-1.6 mL of appropriate solvent to obtain a clear solution in a 3-mL vial. This solution was then placed into a 20-mL vial with 4 mL of volatile solvents. The 20-mL vial was sealed with a cap and kept at RT allowing sufficient time for organic vapor to interact with the solution. Clear solution was obtained after 12 days and transferred to evaporate at RT. The solids were isolated for XRPD analysis. The results summarized in Table 13 showed that Form A, B and amorphous material were observed.

TABLE 13

Summary of vapor-solution diffusion experiments

| Example | Solvent | Anti-solvent | Solid Form |
|---|---|---|---|
| 7-1 | THF | Toluene | Form A |
| 7-2 | DMSO | Toluene | Amorphous |
| 7-3 | Acetone | n-Heptane | Form B |
| 7-4 | 1,4-Dioxane | n-Heptane | Form A |
| 7-5 | ACN | MTBE | Amorphous |
| 7-6 | CHCl$_3$ | MTBE | Amorphous |
| 7-7 | MeOAc | IPAc | Form A |
| 7-8 | 2-MeTHF | IPAc | Form A |

* clear solution was obtained vapor-solution diffusion, the solid was obtained via evaporation at RT.

Examples 8: Preparation of Solid-State Forms by Anti-Solvent Addition Method

A total of 12 anti-solvent addition experiments were carried out. About 20 mg of starting material (Example 1) was dissolved in 0.2-1.6 mL solvent to obtain a clear solution and the solution was magnetically stirred (~1000 rpm) followed by addition of 0.1 mL anti-solvent perstep till precipitate appeared or the total amount of anti-solvent reached 10 mL. The obtained precipitate was isolated for XRPD analysis. Results in Table 14 showed that Form A, Form A+B and amorphous material were generated.

TABLE 14

Summary of anti-solvent addition experiments

| Example | Solvent | Anti-solvent | Solid Form |
|---|---|---|---|
| 8-1* | Acetone | H$_2$O | Form A + B |
| 8-2** | ACN | | Form A + B |

TABLE 14-continued

Summary of anti-solvent addition experiments

| Example | Solvent | Anti-solvent | Solid Form |
|---|---|---|---|
| 8-3** | DMAc | Toluene | Form A + B |
| 8-4** | 1,4-Dioxane | | Form A |
| 8-5* | Acetone | n-Heptane | Form A |
| 8-6 | THF | | Amorphous |
| 8-7* | CHCl$_3$ | MTBE | Amorphous |
| 8-8** | ACN | | Amorphous |
| 8-9** | MeOH | IPAc | Amorphous |
| 8-10** | DMAc | | Form A |
| 8-11** | 2-MeTHF | CPME | Form A |
| 8-12** | MeOAc | | Form A |

*The solid was obtained after 5° C. stirring.
**Clear solution obtained after 5° C. stirring and the solid was obtained via evaporation at RT.

Examples 9: Preparation of Solid-State Forms by Reverse Anti-Solvent Addition Method Reverse anti-solvent addition experiments were conducted under 10 conditions. Approximately 15 mg of starting material (Example 1) was dissolved in 0.2-1.8 mL of each solvent to get a clear solution. This solution was added drop-wise into a glass vial containing 5 mL of each anti-solvent at RT. The precipitate was isolated for XRPD analysis. The results summarized Table 15 showed that Form A, Form A+B, and amorphous material were obtained.

TABLE 15

Summary of reverse anti-solvent addition experiments

| Example | Solvent | Anti-solvent | Solid Form |
|---|---|---|---|
| 9-1 | MeOH | H$_2$O | Amorphous |
| 9-2 | DMAc | | Amorphous |
| 9-3** | ACN | Toluene | Amorphous |
| 9-4** | DMSO | | Form A + B |
| 9-5 | CHCl$_3$ | n-Heptane | Amorphous |
| 9-6 | MeOAc | | Form A |
| 9-7* | DCM | MTBE | Amorphous |
| 9-8** | Acetone | IPAc | Amorphous |
| 9-9** | 2-MeTHF | | Amorphous |
| 9-10** | THF | CPME | Form A |

*The solid was obtained after 5° C. stirring.
**Clear solution obtained after 5° C. stirring and the solid was obtained via evaporation at RT.

Examples 10: Preparation of Solid-State Forms by Slow Evaporation Method

Slow evaporation experiments were performed under 12 conditions. Around 15 mg of starting material (Example 1) was dissolved in 0.4-2.0 mL of solvent in a 3-mL glass vial. If not dissolved completely, suspensions were filtered using a PTFE membrane (pore size of 0.45 m) to give clear solutions, which were subjected to evaporation at RT with vials sealed by Parafilm® (poked with 3 pin-holes). The solids were formed during evaporation and were isolated for XRPD analysis, and the results summarized in Table 16 indicated that Form A, Form A+B, and amorphous material were obtained.

TABLE 16

Summary of slow evaporation experiments

| Example | Solvent (v/v) | Solid Form |
|---|---|---|
| 10-1 | MeOH | Form A |
| 10-2 | Acetone | Form A |
| 10-3 | THF | Amorphous |
| 10-4 | 2-MeTHF | Form A |
| 10-5 | ACN | Form A + B |
| 10-6 | DCM | Amorphous |
| 10-7 | CHCl$_3$ | Amorphous |
| 10-8 | MeOAc | Form A |
| 10-9 | Acetone/Toluene (4:1) | Amorphous |
| 10-10 | THF/H$_2$O (4:1) | Form A + B |
| 10-11 | ACN/H$_2$O (4:1) | Amorphous |
| 10-12 | MeOH/IPAc (4:1) | Form A |

Example 11: Preparation of Form a of Compound (I)

Form A was alternatively prepared by adding 10 g of Compound (I) to anhydrous toluene (80 mL) at RT. The mixture was heated at 80° C. to dissolve the material and was then cooled to 60° C. and was kept at 60° C. overnight. The mixture was gradually cooled to RT, and the mixture was stirred at RT for about 18 hours. The solid was collected by vacuum filtration, washed with toluene, and dried by pulling air though the filter for 1 hour to provide the desired product as a white crystalline sold, which was characterized by XRPD, TGA and DSC. XRPD of Example 11 is consistent with FIG. 1. TGA and DSC of Example 11 are consistent with FIG. 2, so Example 11 was also Form A.

Example 12: Preparation of Form B by Slurry at 50° C. Method

About 15 mg of starting material (Example 1) was suspended in 0.5 mL of IPAc in an HPLC vial. After the suspension was magnetically stirred (~1000 rpm) for about 4 days at 50° C., the solid was isolated for XRPD analysis (Example 12). The XRPD pattern and TGA/DSC curves of Example 12 are consistent with FIG. 3 and FIG. 4 respectively. A weight loss of 1.0% up to 150° C. and an endotherm at 188.7° C. (onset temperature) were observed on the TGA/DSC curves.

Example 13: Preparation of Form B by Slurry Cycling (50-5° C.) and Slurry at 50° C. Method Example 13 was prepared via temperature cycling from 50° C. to 5° C. in H$_2$O, followed by slurry at 50° C. for 1 day. The XRPD pattern of Example 13 is consistent with FIG. 3, so Example 13 was Form B.

Example 14: Preparation of Singly Crystal by Slow Evaporation

First, 5.1 mg of compound (Example 1) starting material was weighed into a 3-mL glass vial followed by addition of 0.35 mL MeOH. After being oscillated on a vortex and ultrasonically shaken to accelerate dissolution, the solution was then filtered through PTFE filter membrane (0.45 μm) and disposable syringe to a 4-mL shell vial (44.6 mm×14.65 mm). A little amount of crystal sample (Example 10-1) was added to the vial as crystal seed and then the vial was covered using PE-Plug with one pinhole on it for slow evaporation at RT. After 5 days, rod-like single crystals were obtained.

Example 15: Preparation of Form C of Compound (I)

A crystalline form of Compound (I) was obtained via evaporation of DCM solution at RT for 1 day, followed by drying at RT. The XRPD pattern and TGA/DSC curves are shown in FIG. 5 and FIG. 7. As displayed in FIG. 5, XRPD revealed that Example 15 is crystalline and thus named as Form C.

Alternatively, Form C was prepared by slow-cooling method. A solution of Compound (I) in methanol-water was heated to about 50° C. The hot mixture was filtered and the filtrate was slowly cooled to 5° C. The precipitated solids were filtered and the resulting solids were mixed with water for several days. The resulting slurry was filtered to provide Form C.

The crystalline Form C is characterized by having the X-ray powder diffraction displaying peaks expressed as 2-theta degree at about 9.8, 10.2, 14.8, 15.2 and 20.4 (each time plus or minus 0.2), which optionally further shows the following peaks expressed as 2-theta degrees at: about 18.1 and 22.3 (each time plus or minus 0.2), optionally further characterized by a powder X-ray diffractogram as substantially illustrated in FIG. 5 and its characteristic signals are summarized in the following Table 17.

Figure 6:
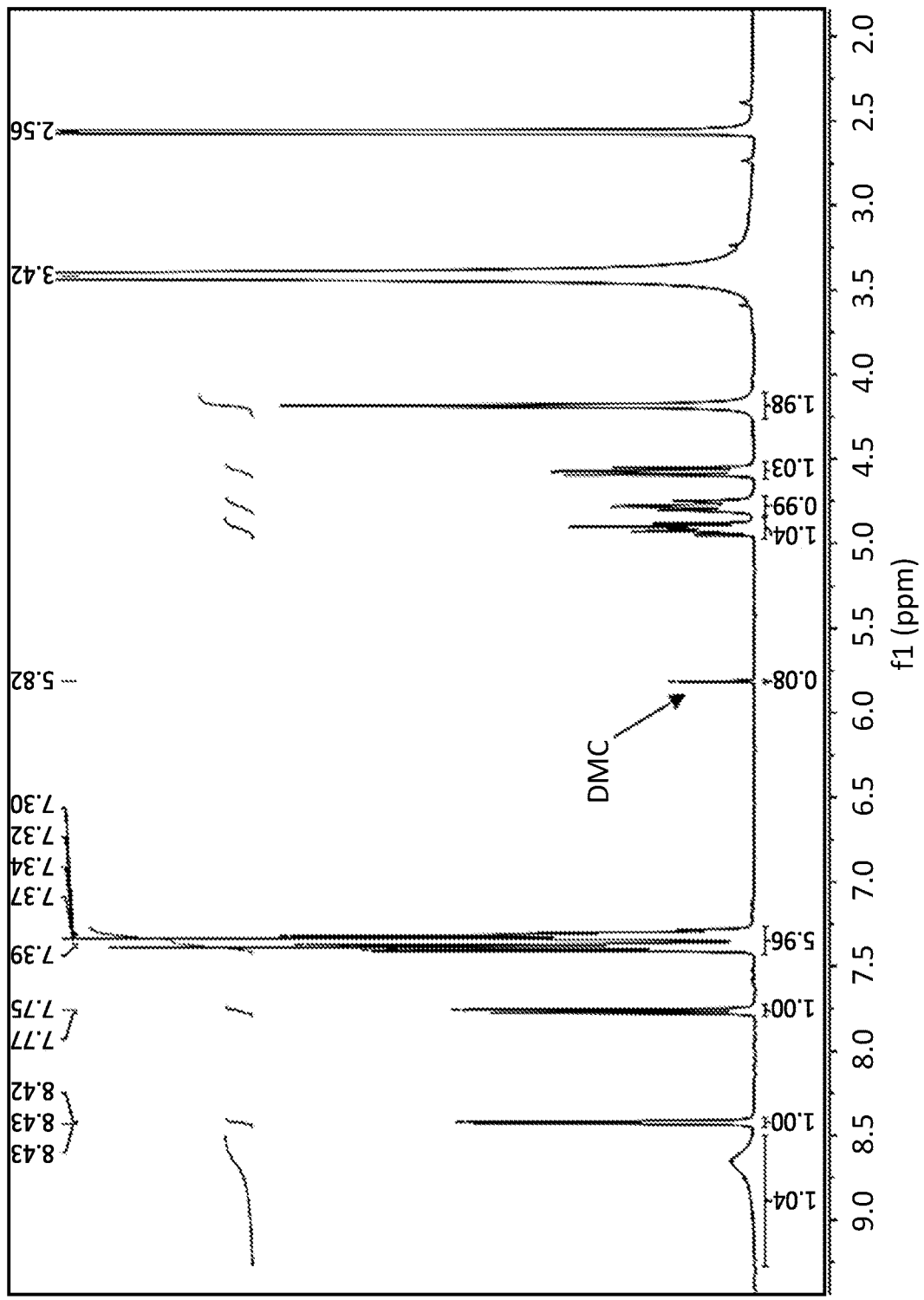
FIG. 6 is $^1$HNMR spectrum of Form C of Compound (I).

A weight loss of 5.7% up to 100° C. was observed on the TGA curve for Form C prepared by evaporation. The DSC data showed two endotherms at 80.9° C. (peak temperature) and 124.9° C. (onset temperature). H NMR in FIG. 6 indicated that DCM solvent was observed and the molar ratio of DCM: freeform was ~0.04:1 (0.9 wt %). XRPD comparison pattern indicated that no form change was observed for Form C after heated to 100° C. and cooled to RT. TGA and DSC results of Form C after heated showed a weight loss of 2.5% up to 100° C. on the TGA curve, while two endotherms at 76.5° C. (peak temperature) and 127.0° C. (onset temperature) were observed on the DSC curve. For form identification, variable-temperature XRPD (VT-XRPD) was performed for Form C. The XRPD patterns indicated that no change was observed after heating Form C to 100° C. under $N_2$. Considering the large TGA weight loss and no XRPD change after removal of water/solvent (VT-XRPD). Single crystal structure determination confirmed that Form C is a channel hydrate (without form change after dehydration).

TABLE 17

| XRPD Peak list of Form C | | |
|---|---|---|
| Pos. [°2Th.] (±0.2) | d-spacing [Å] | Rel. Int. [%] |
| 9.8 | 9.00 | 100.00 |
| 10.2 | 8.68 | 30.84 |
| 13.6 | 6.51 | 4.09 |
| 14.8 | 5.98 | 5.57 |
| 15.2 | 5.82 | 7.88 |
| 18.1 | 4.91 | 11.03 |
| 18.5 | 4.81 | 5.33 |
| 19.3 | 4.60 | 5.46 |
| 19.7 | 4.50 | 3.55 |
| 20.4 | 4.34 | 22.13 |
| 21.3 | 4.17 | 3.18 |
| 21.6 | 4.11 | 3.47 |

TABLE 17-continued

| XRPD Peak list of Form C | | |
|---|---|---|
| Pos. [°2Th.] (±0.2) | d-spacing [Å] | Rel. Int. [%] |
| 21.9 | 4.06 | 3.60 |
| 22.3 | 3.99 | 8.25 |
| 24.6 | 3.62 | 3.76 |
| 25.8 | 3.45 | 1.87 |
| 28.9 | 3.09 | 1.97 |
| 30.9 | 2.89 | 3.52 |

Example 16: Preparation of Form D-IPA Solvate

Generally following the procedure described in Example 6, a crystalline form of Compound (I) was obtained via vapor-solid diffusion of Form C of Compound (I) in IPA for about 6 days. As displayed in FIG. 8, XRPD revealed that Example 16 is crystalline and thus named as Form D. The crystalline Form D of Compound (I), characterized by having the X-ray powder diffraction displaying peaks expressed as 2-theta degree at about 8.2, 10.4, 12.1 and 16.3 (each time plus or minus 0.2), which optionally further shows the following peaks expressed as 2-theta degrees at: about 19.9 and 21.0 (each time plus or minus 0.2), optionally further characterized by a powder X-ray diffractogram as substantially illustrated in FIG. 8 and its characteristic signals are summarized in the following Table 18.

The TGA/DSC curves are shown in FIG. 9. A two-stage weight loss of 3.8% up to 85° C. and 11.5% from 85° C. to 120° C. was observed on the TGA curve. The DSC data showed one endotherm at 93° C. (onset temperature). $^1$H NMR indicated that IPA solvent was observed and the molar ratio of IPA: freeform was 0.8:1 (11.3 wt %) in Form D, which corresponded to the second-stage weight loss on TGA (FIG. 10). For form identification, Form D was heated to 100° C. and cooled to RT. As XRPD comparison show that D sample converted to Form C after heated and cooled to RT. According to the results, Form D was characterized to be an IPA solvate.

TABLE 18

| XRPD Peak list of Form D | | |
|---|---|---|
| Pos. [°2Th.] (±0.2) | d-spacing [Å] | Rel. Int. [%] |
| 8.2 | 10.85 | 100.00 |
| 9.8 | 9.05 | 2.88 |
| 10.4 | 8.51 | 17.87 |
| 12.1 | 7.29 | 13.84 |
| 15.1 | 5.86 | 5.90 |
| 15.5 | 5.72 | 3.66 |
| 16.3 | 5.43 | 19.12 |
| 16.8 | 5.28 | 2.28 |
| 18.0 | 4.93 | 1.01 |
| 18.8 | 4.73 | 4.75 |
| 19.9 | 4.47 | 9.89 |
| 21.0 | 4.24 | 5.17 |
| 21.6 | 4.11 | 4.90 |
| 22.7 | 3.92 | 7.11 |
| 23.6 | 3.78 | 6.15 |
| 23.9 | 3.72 | 4.75 |
| 24.4 | 3.64 | 3.99 |
| 24.8 | 3.60 | 3.26 |
| 25.9 | 3.44 | 0.93 |
| 26.8 | 3.32 | 1.50 |
| 27.6 | 3.23 | 2.52 |
| 28.4 | 3.14 | 3.14 |

TABLE 18-continued

XRPD Peak list of Form D

| Pos. [°2Th.] (±0.2) | d-spacing [Å] | Rel. Int. [%] |
|---|---|---|
| 29.3 | 3.05 | 0.80 |
| 29.9 | 2.99 | 3.31 |
| 30.6 | 2.92 | 0.80 |
| 31.6 | 2.84 | 1.06 |
| 36.8 | 2.44 | 0.25 |

Example 17: Preparation of Form E-DCM Solvate 15 mg of starting material (Example 1) was dissolved in 0.4-2.0 mL of DCM in a 3-mL glass vial. The suspension was filtered using a PTFE membrane (pore size of 0.45 m) and the filtrate was subjected to evaporation at RT with vials sealed by Parafilm® (poked with 3 pin-holes). Some solid was observed in the solution. The XRPD pattern of wet sample (covered with a plastic film when testing XRPD) is shown in FIG. 11 and the form is characterized as Form E. The DCM solvate form E of Compound (I) is characterized by having the X-ray powder diffraction displaying peaks expressed as 2-theta degrees at about 9.5, 17.1, 20.1, 20.6 and 24.6 (each time plus or minus 0.2), which optionally further shows the following peaks expressed as 2-theta degrees at: about 8.11, 10.0 and 30.1 (each time plus or minus 0.2), optionally further characterized by a powder X-ray diffractogram as substantially illustrated in FIG. 11.

The characteristic X-ray powder diffractogram of the DCM solvate Form E of Compound (I) can be given substantially in FIG. 11 and its characteristic signals are summarized in the following Table 19.

The XRPD comparison shown Form E converted to Form C once exposed to ambient condition. Therefore, TGA and DSC characterizations were not performed for Form E. According to the single crystal structure determination results, Form E is a DCM solvate.

TABLE 19

XRPD Peak list of Form E

| Pos. [°2Th.] (±0.2) | d-spacing [Å] | Rel. Int. [%] |
|---|---|---|
| 8.1 | 10.91 | 19.88 |
| 9.5 | 9.35 | 100.00 |
| 10.0 | 8.87 | 34.86 |
| 10.2 | 8.64 | 6.66 |
| 12.2 | 7.25 | 4.52 |
| 13.1 | 6.75 | 7.29 |
| 14.9 | 5.94 | 20.61 |
| 16.2 | 5.46 | 11.31 |
| 17.1 | 5.18 | 52.32 |
| 17.6 | 5.04 | 12.82 |
| 18.6 | 4.76 | 3.55 |
| 19.0 | 4.68 | 13.03 |
| 19.4 | 4.57 | 3.90 |
| 20.1 | 4.43 | 30.06 |
| 20.6 | 4.31 | 29.18 |
| 21.1 | 4.22 | 10.25 |
| 22.1 | 4.03 | 21.41 |
| 23.0 | 3.87 | 17.08 |
| 24.6 | 3.63 | 30.48 |
| 28.0 | 3.18 | 14.70 |
| 28.9 | 3.09 | 6.98 |
| 30.1 | 2.97 | 18.84 |

Example 18: Preparation of Form F-MeOH Solvate

Generally following the procedure described in Example 4, Example 18 could be obtained via slow cooling (50° C. to 5° C.) from MeOH or MeOH/H$_2$O (19:1) solutions. The single crystal structure determination results indicated that Form F was a MeOH solvate, and the calculated XRPD pattern of Form F is shown in FIG. 12. The MeOH solvate form F of Compound (I) is characterized by having the X-ray powder diffraction displaying peaks expressed as 2-theta degrees at about 9.8, 10.2, 17.8, 22.3 and 24.9 (each time plus or minus 0.2), which optionally further shows the following peaks expressed as 2-theta degrees at: about 20.9, 21.1 and 21.8 (each time plus or minus 0.2), optionally further characterized by a powder X-ray diffractogram as substantially illustrated in FIG. 12.

The characteristic X-ray powder diffractogram of the MeOH solvate Form F of Compound (I) can be given substantially in FIG. 12 and its characteristic signals are summarized in the following Table 20. The experimental XRPD, TGA and DSC data were not collected for Form F.

TABLE 20

XRPD Peak list of Form F

| Pos. [°2Th.] (±0.2) | d-spacing [Å] | Rel. Int. [%] |
|---|---|---|
| 5.1 | 17.25503 | 1.37 |
| 6.2 | 14.22047 | 0.36 |
| 7.4 | 11.89379 | 0.55 |
| 8.1 | 10.85370 | 2.15 |
| 8.7 | 10.12322 | 0.66 |
| 9.8 | 9.03663 | 100.00 |
| 10.2 | 8.68810 | 48.42 |
| 11.6 | 7.63523 | 0.29 |
| 12.1 | 7.32855 | 0.87 |
| 12.4 | 7.13008 | 1.38 |
| 13.5 | 6.54075 | 8.89 |
| 15.3 | 5.80141 | 25.99 |
| 16.3 | 5.42688 | 10.34 |
| 17.8 | 4.97 | 35.08 |
| 18.3 | 4.84 | 13.25 |
| 18.8 | 4.71 | 16.17 |
| 19.2 | 4.63 | 12.00 |
| 19.6 | 4.52 | 4.62 |
| 20.2 | 4.40 | 8.55 |
| 20.4 | 4.34 | 18.00 |
| 20.9 | 4.26 | 29.05 |
| 21.2 | 4.20 | 25.06 |
| 21.8 | 4.08 | 24.83 |
| 22.3 | 3.98 | 36.28 |
| 23.7 | 3.76 | 1.92 |
| 24.2 | 3.68 | 3.91 |
| 24.9 | 3.57 | 37.96 |
| 26.0 | 3.42 | 20.52 |
| 26.3 | 3.38 | 4.27 |
| 27.4 | 3.26 | 2.54 |
| 27.9 | 3.20 | 2.26 |
| 28.1 | 3.17 | 2.04 |
| 28.8 | 3.10 | 6.14 |
| 29.4 | 3.04 | 2.97 |
| 29.9 | 2.98 | 6.15 |
| 30.8 | 2.90 | 21.34 |
| 31.6 | 2.83 | 1.64 |
| 32.1 | 2.78 | 0.96 |
| 32.9 | 2.72 | 2.19 |
| 33.3 | 2.69 | 1.48 |
| 33.6 | 2.67 | 4.59 |
| 34.0 | 2.63 | 3.61 |
| 34.6 | 2.59 | 2.00 |
| 35.1 | 2.55 | 2.73 |
| 36.0 | 2.50 | 1.10 |
| 36.4 | 2.47 | 1.02 |
| 36.8 | 2.44 | 1.30 |

TABLE 20-continued

XRPD Peak list of Form F

| Pos. [°2Th.] (±0.2) | d-spacing [Å] | Rel. Int. [%] |
|---|---|---|
| 37.8 | 2.38 | 1.10 |
| 38.3 | 2.35 | 4.79 |
| 39.2 | 2.29 | 1.72 |
| 39.6 | 2.27 | 1.28 |

Example 19: Inter-Conversion Study of Crystal Forms

To understand the thermodynamic stability relationship between Form A, B and C, slurry competition experiments in $H_2O$ and n-Heptane were performed at RT and 70° C. Prior to the study, the starting material (Form A of Compound (I)) was used to saturate the corresponding solvent at RT and 70° C. before filtered to obtain a near-saturated solution. Equal amounts (~ 5 mg) of Form A, Form B and Form C were weighed and then added to 0.3 mL of the prepared solution to form a new suspension, which was stirred magnetically (~1000 rpm) at RT/70° C. for about 2 days. As summarized in Table 21, Form B was obtained in 4 conditions, indicating Form B was thermodynamically more stable than Form A and C from RT to 70° C. At room temperature (RT, 25±2° C.) and 70° C., Form A and Form C converted to Form B after slurry in $H_2O$ and n-Heptane for 2 days, indicating Form B was the thermodynamically more stable form among Form A/B/C from RT to 70° C. Detailed inter-conversion relationship can be referred to the schematic diagram shown in FIG. 13.

TABLE 21

Summary of slurry competition experiments

| Experiment | Starting form | Solvent | Temperature | Crystal form |
|---|---|---|---|---|
| 1 | Form A + B + C | $H_2O$ | RT | Form B |
| 2 | | n-Heptane | | |
| 3 | | $H_2O$ | 70° C. | |
| 4 | | n-Heptane | | |

Example 20: Dynamic Vapor Sorption (DVS)

To investigate the solid form stability as a function of humidity, DVS isotherm plots of Form A, Form B, and Form C were collected at 25° C. between 0 and 95% RH. All the samples were characterized using XRPD after DVS test and no form change was observed.

As determined by Dynamic Vapor Sorption (DVS) in the range of from 0 percent to 95 percent relative humidity at a temperature of about 25 degrees centigrade (plus or minus 0.2 degrees C.), the crystalline Form A, Form B, and Form C of Compound (I) show a weight gain of about 0.09 weight percent, 0.07 weight percent, and 5.7 weight percent, respectively.

The term "no hygroscopicity" as used herein refers to compound showing a weight gain of less than 0.2 weight percent based on the weight of the compound when measured in the range of from 0 to 95 percent relative humidity at about 25 degrees centigrade (plus or minus 0.2 degrees C.). Thus, these results demonstrate that the crystalline Form A and Form B of Compound (I) displays no hygroscopicity.

Example 21: Physical and Chemical Stability

To evaluate the physical and chemical stability, Form A, Form B, and Form C were stored in 3 conditions (40° C./75% RH; 25° C./60% RH; and 60° C.) for two and four weeks. All samples were characterized using XRPD and HPLC. XRPD results indicated no observable form change. HPLC result indicated that no noticeable HPLC purity change was observed.

Example 22: Kinetic Solubility

Kinetic solubility tests of Form A, Form B, and Form C was performed in bio-relevant media (SGF, FaSSIF and FeSSIF) and $H_2O$ at 37° C. Solids were suspended into FaSSIF, FeSSIF, SGF and $H_2O$ with target conc. of ~10 mg/mL. The suspensions were agitated on a rolling incubator at 25 rpm (in the incubator set at 37° C.) for 1, 4 and 24 hrs. At each time point, 1 mL of the suspension was pipetted out for centrifugation at 25000 rpm (3 min) and filtration through 0.45 μm membrane to obtain supernatant for HPLC solubility and pH tests. The residual solids were analyzed by XRPD. No form change was observed for Form A and Form B after kinetic solubility test in bio-relevant media or $H_2O$, while Form C sample converted to Form A after solubility test. The solubility of Form A/B/C was summarized from Table 22-24.

TABLE 22

Summary of kinetic solubility results of Form A

| Initial Form | Media | Time (hr) | Final Form | Solubility (mg/mL) | Observation | Final pH |
|---|---|---|---|---|---|---|
| A | SGF (pH 1.8) | 1 | A | 0.10 | Turbid | 1.9 |
| | | 4 | A | 0.10 | Turbid | 2.0 |
| | | 24 | A | 0.10 | Turbid | 1.9 |
| | FaSSIF (pH 6.5) | 1 | A | 0.10 | Turbid | 6.3 |
| | | 4 | A | 0.10 | Turbid | 6.4 |
| | | 24 | A | 0.10 | Turbid | 6.5 |
| | FeSSIF (pH 5.0) | 1 | A | 0.12 | Turbid | 4.9 |
| | | 4 | A | 0.12 | Turbid | 4.9 |
| | | 24 | A | 0.12 | Turbid | 4.9 |
| | $H_2O$ (pH 6.5) | 1 | A | 0.08 | Turbid | 6.5 |
| | | 4 | A | 0.09 | Turbid | 7.0 |
| | | 24 | A | 0.09 | Turbid | 5.3 |

TABLE 23

Summary of kinetic solubility results of Form B

| Initial Form | Media | Time (hr) | Final Form | Solubility (mg/mL) | Observation | Final pH |
|---|---|---|---|---|---|---|
| B | SGF (pH 1.8) | 1 | B | 0.08 | Turbid | 1.9 |
| | | 4 | B | 0.08 | Turbid | 2.0 |
| | | 24 | B | 0.08 | Turbid | 1.8 |
| | FaSSIF (pH 6.5) | 1 | B | 0.08 | Turbid | 6.3 |
| | | 4 | B | 0.09 | Turbid | 6.5 |
| | | 24 | B | 0.09 | Turbid | 6.4 |
| | FeSSIF (pH 5.0) | 1 | B | 0.10 | Turbid | 4.9 |
| | | 4 | B | 0.11 | Turbid | 4.9 |
| | | 24 | B | 0.10 | Turbid | 4.9 |
| | $H_2O$ (pH 6.5) | 1 | B | 0.07 | Turbid | 5.5 |
| | | 4 | B | 0.07 | Turbid | 7.3 |
| | | 24 | B | 0.07 | Turbid | 6.2 |

TABLE 24

Summary of kinetic solubility results of Form C

| Initial Form | Media | Time (hr) | Final Form | Solubility (mg/mL) | Observation | Final pH |
|---|---|---|---|---|---|---|
| C | SGF (pH 1.8) | 1 | A | 0.70 | Turbid | 2.0 |
|   |   | 4 | A | 0.11 | Turbid | 2.0 |
|   |   | 24 | A | 0.10 | Turbid | 1.8 |
|   | FaSSIF (pH 6.5) | 1 | C | 0.86 | Turbid | 6.3 |
|   |   | 4 | C | 0.73 | Turbid | 6.5 |
|   |   | 24 | A | 0.15 | Turbid | 6.5 |
|   | FeSSIF (pH 5.0) | 1 | C | 0.97 | Turbid | 4.9 |
|   |   | 4 | A | 0.15 | Turbid | 4.9 |
|   |   | 24 | A | 0.17 | Turbid | 4.9 |
|   | $H_2O$ (pH 6.5) | 1 | A + C | 0.44 | Turbid | 6.1 |
|   |   | 4 | A | 0.10 | Turbid | 7.5 |
|   |   | 24 | A | 0.10 | Turbid | 5.9 |

Example 23: Equilibrium Solubility

Equilibrium solubility of Form B was measured in 8 pH buffers (i.e., pH 1.0, 2.0, 3.0, 4.0, 5.0, 6.0, 7.0, 8.0) at RT for 24 hrs. Solids were suspended into pH buffers with target conc. of ~10 mg/mL. The suspensions were slurried at RT for 24 hrs (1000 rpm), prior to centrifugation at 20000 rpm (2 min), and filtration through 0.45 μm membrane to obtain supernatant for HPLC solubility and pH tests. The residual solids were analyzed by XRPD. No form change was observed for Form B after solubility evaluation in pH buffers.

Example 24: Single Crystal Structure Determination of Form B

A suitable single crystal with good diffraction quality was selected out from the rod-like crystal samples (Example 14) and was mounted on a mylar loop in a random orientation and immersed in a stream of nitrogen at 175 K. Preliminary examination and data collection were performed on a Bruker D8 VENTURE diffractometer (Mo/Kα radiation, λ=0.71073 Å) and analyzed with the APEX3 software package.

Cell parameters and an orientation matrix for data collection were retrieved and refined (least-squares refinement) by SAINT (Bruker, V8.37A) software using the setting angles of 9086 reflections in the range 2.217°<θ<27.401°. The data were collected to a maximum diffraction angle (θ) of 27.549° at 175K. The data set was 99.30% complete out to 27.549° in θ, having a Mean I/σ of 15.3 and D min (Mo) of 0.77 Å.

A multi-scan absorption correction was performed using SADABS-2014/5 (Bruker, 2014/5.) $wR_2$(int) was 0.1401 before and 0.0825 after correction. The absorption coefficient μ of this material is 0.100 $mm^{-1}$ at this wavelength (/∴=0.71073 Å) and the minimum and maximum transmissions are 0.5818 and 0.7456 Intensities of equivalent reflections were averaged. The agreement factor for the averaging was 5.22% based on intensity.

The structure was solved in the space group $P2_1$ by Intrinsic Phasing using the ShelXT[1] structure solution program and refined by Least Squares using version 2017/1 of ShelXL[2] (Sheldrick, 2015) refinement package contained in OLEX2[3]. All non-hydrogen atoms were refined anisotropically. The positions of hydrogen atoms were refined freely according to the Fourier Map.

The crystal system is monoclinic and the space group is $P2_1$. The cell parameters are: a=5.0418(8) Å, b=15.320(3) Å, c=11.599(2) Å, α=90°, β=98.383(5°), γ=90°, V=886.3(3) $Å^3$. The formula weight is 378.39 g·$mol^{-1}$ with Z=2, resulting in the calculated density of 1.418 g·$cm^{-3}$ (Table 25).

TABLE 25

Crystallographic data of Form B at 175 K

| | |
|---|---|
| Crystal system, space group | monoclinic, $P2_1$ |
| Unit cell dimensions | a = 5.0418(8) Å |
| | b = 15.320(3) Å |
| | c = 11.599(2) Å |
| | α = 90° |
| | β = 98.383(5)° |
| | γ = 90° |
| Volume | 886.3(3) $Å^3$ |
| Z, Calculated density | 2, 1.418 g/$cm^3$ |
| Reflections collected/ Independent reflections | 14269/4034 [$R_{int}$ = 0.0522, $R_{sigma}$ = 0.0494] |

The thermal ellipsoids drawing of the compound in the crystal lattice is shown in FIG. 14. The hydrogen bonds in the single crystal structure are shown in FIG. 15 and Table 26. The calculated XRPD generated from the single crystal structure data and the experimental XRPD pattern of the single crystal sample are consistent with Compound (I) Form B reference as shown in FIG. 16.

TABLE 26

H-bonds list for the Compound (I) Form B single crystal

| D-H . . . A | Type | d(D . . . H)/ Å | d(H . . . A)/ Å | d(D . . . A)/ Å | (D-H . . . A)/° |
|---|---|---|---|---|---|
| N1-H1 . . . N2[#1] | Intermolecular | 0.88(3) | 2.57(3) | 3.311(3) | 143(2) |
| N1-H1 . . . N3[#1] | Intermolecular | 0.88(3) | 2.06(3) | 2.928(3) | 172(2) |
| N4-H4 . . . O1[#2] | Intermolecular | 0.83(2) | 2.25(3) | 2.948(3) | 142(2) |
| N4-H4 . . . N3 | Intramolecular | 0.83(2) | 2.54(3) | 2.863(3) | 105(2) |

Example 25: Single Crystal Structure Determination of Form E

A suitable single crystal with good diffraction quality was selected out from the block-like crystal samples and was analyzed by single-crystal X-ray diffractometry.

Cell parameters and an orientation matrix for data collection were retrieved and refined (least-squares refinement) by SAINT (Bruker, V8.37A, after 2013) software using the setting angles of 4176 reflections in the range 2.907°<θ<24.230°. The data were collected to a maximum diffraction angle (θ) of 27.506° at 175K. The data set was 98.4% complete out to 27.506° in θ, having a Mean I/σ of 7.2 and D min (Mo) of 0.77 Å.

Frames were integrated with SAINT (Bruker, V8.374, after 2013). A total of 14827 reflections were collected, of which 4858 were unique. Lorentz and polarization corrections were applied to the data. A multi-scan absorption correction was performed using SADABS-2014/5 (Bruker, 2014/5). wR$_2$(int) was 0.1189 before and 0.0837 after correction. The absorption coefficient µ of this material is 0.337 mm$^{-1}$ at this wavelength (/∴=0.71073 Å) and the minimum and maximum transmissions are 0.5036 and 0.7456. Intensities of equivalent reflections were averaged. The agreement factor for the averaging was 8.52% based on intensity.

The structure was solved in the space group P2$_1$2$_1$2$_1$ by Intrinsic Phasing method using the ShelXT[4] structure solution program and refined by Least Squares using version 2017/1 of ShelXL[2] (Sheldrick, 2015) refinement package contained in OLEX2[3]. All non-hydrogen atoms were refined anisotropically. The positions of hydrogen atoms residing on carbon atoms were calculated geometrically and refined using the riding model, but the hydrogen atoms residing on nitrogen were refined freely according to the Fourier Map.

The structure of the crystal was determined successfully. The crystal system is orthorhombic and the space group is P2$_1$2$_1$2$_1$. The cell parameters are: a=9.5908(13) Å, b 10.2639(16) Å, c=21.863(3) Å, α=90°, β=90°, γ=90°, V=2152.2(5) Å, The formula weight is 463.32 g·mol$^{-1}$ with Z=4, resulting in the calculated density of 1.430 g·cm$^{-3}$ (Table 27).

The asymmetric unit of the single crystal structure is comprised of one Compound (I) molecule and one DCM solvent molecule indicating the crystal is a DCM solvate of Compound (I). The thermal ellipsoids drawing of the Compound (I) molecule and DCM solvent molecule in the crystal lattice are shown in FIG. 17. The single crystal structure determination confirmed the absolute configuration assignment (R/S) of the chiral atom in the compound as C11(S). The calculated XRPD generated from the single crystal structure data is shown in FIG. 18

TABLE 27

Crystal Data of Compound I (Form E) at 175 K

| | |
|---|---|
| Crystal system, space group | Orthorhombic, P2$_1$2$_1$2$_1$ |
| Unit cell dimensions | a = 9.5908(13) Å |
| | b = 10.2639(16) Å |
| | c = 21.863(3) Å |
| | α = 90° |
| | β = 90° |
| | γ = 90° |
| Volume | 2152.2(5) Å$^3$ |
| Z, Calculated density | 4, 1.430 g/cm$^3$ |
| Reflections collected/ Independent reflections | 14827/4858 [R$_{int}$ = 0.0852, R$_{sigma}$ = 0.0945] |

CONCLUSION

As shown the above-described results of DSC and DVS, the anhydrate crystalline Form B and Form A have higher melting point and are less hygroscopic compared to Form C and Forms D, Form E and Form F. From slurry competition experiments shown above, Form A and Form C converted to Form B after slurry in H$_2$O and n-Heptane for 2 days, indicating Form B was the thermodynamically more stable form among Form A, Form B, and Form C from RT to 70° C.

The anhydrate crystalline Form B of Compound (I) appears thus to be the most suitable product for use and storage at an industrial scale. Indeed, the anhydrate crystalline Form B of Compound (I) is not hygroscopic and stable (value of melting point) as indicated above.

What is claimed is:

1. A crystalline form selected from the group consisting of:
   Form A of (S)-5-benzyl-N-(5-methyl-4-oxo-2,3,4,5-tetrahydropyrido [3,2-b][1,4]oxazepin-3-yl)-4H-1,2,4-triazole-3-carboxamide;
   Form B of (S)-5-benzyl-N-(5-methyl-4-oxo-2,3,4,5-tetrahydropyrido [3,2-b][1,4]oxazepin-3-yl)-4H-1,2,4-triazole-3-carboxamide;
   Form C of (S)-5-benzyl-N-(5-methyl-4-oxo-2,3,4,5-tetrahydropyrido [3,2-b][1,4]oxazepin-3-yl)-4H-1,2,4-triazole-3-carboxamide;
   Form D of (S)-5-benzyl-N-(5-methyl-4-oxo-2,3,4,5-tetrahydropyrido [3,2-b][1,4]oxazepin-3-yl)-4H-1,2,4-triazole-3-carboxamide;
   Form E of (S)-5-benzyl-N-(5-methyl-4-oxo-2,3,4,5-tetrahydropyrido [3,2-b][1,4]oxazepin-3-yl)-4H-1,2,4-triazole-3-carboxamide; and
   Form F of (S)-5-benzyl-N-(5-methyl-4-oxo-2,3,4,5-tetrahydropyrido [3,2-b][1,4]oxazepin-3-yl)-4H-1,2,4-triazole-3-carboxamide.

2. A crystalline form of (S)-5-benzyl-N-(5-methyl-4-oxo-2,3,4,5-tetrahydropyrido [3,2-b][1,4]oxazepin-3-yl)-4H-1,2,4-triazole-3-carboxamide, characterized as Form A.

3. The crystalline form of claim 2, having an X-ray powder diffraction pattern derived using Cu (Kα) radiation comprising three, four, five, six, seven or more peaks, in terms of 2-theta degrees, selected from the group consisting of: 6.9, 11.5, 13.0, 13.9, 16.6, 19.4, 23.4, and 24.0±0.2 degrees.

4. The crystalline form of claim 2, having an X-ray powder diffraction pattern substantially in accordance with that shown in FIG. 1.

5. The crystalline form of claim 2, characterized by a differential scanning calorimetry (DSC) curve with an onset at about 186.7° C. and an endothermic peak at 188.9° C.

6. The crystalline form of claim 2, characterized as having one or more of:
   a) an X-ray powder diffraction (XRPD) pattern substantially the same as shown in FIG. 1;
   b) an X-ray powder diffraction (XRPD) pattern derived using Cu(Kα) radiation with peaks, in terms of 2-theta degrees, at about 6.9, 13.0, 16.6, and 23.4±0.2 degrees;
   c) a Differential Scanning calorimetry (DSC) thermogram substantially the same as shown in FIG. 2;
   d) a Differential Scanning calorimetry (DSC) thermogram with three endothermic events having an onset at about 186.7° C. and a peak at about 188.9° C.
   e) a Thermogravimetric Analysis (TGA) pattern substantially the same as shown in FIG. 2;
   f) a Thermogravimetric Analysis (TGA) pattern with an about 1.0% w/w loss from about 27.8° C. to about 150° C.; or
   g) combinations thereof.

7. A crystalline form of (S)-5-benzyl-N-(5-methyl-4-oxo-2,3,4,5-tetrahydropyrido [3,2-b][1,4]oxazepin-3-yl)-4H-1,2,4-triazole-3-carboxamide, characterized as Form B.

8. The crystalline form of claim 7, having an X-ray powder diffraction pattern comprising a peak, in term of 2-theta degree, at about 9.6 and 16.4±0.2 degrees.

9. The crystalline form of claim 7, having an X-ray powder diffraction pattern derived using Cu(Kα) radiation comprising three, four, five, six or more peaks, in terms of degrees, selected from the group consisting of: 9.6, 11.5, 13.8, 16.4, 19.2, 23.2, and 23.8±0.2 degrees.

10. The crystalline form of claim 7, having an X-ray powder diffraction pattern substantially in accordance with that shown in FIG. 3.

11. The crystalline form of claim 7, characterized by a differential scanning calorimetry (DSC) curve comprising an endotherm at about 189.2° C. and an endothermic peak at 191.9° C.

12. The crystalline form of claim 7, characterized as having one or more of:
    a) an X-ray powder diffraction (XRPD) pattern substantially the same as shown in FIG. 3;
    b) an X-ray powder diffraction (XRPD) pattern derived using Cu(Kα) radiation with peaks, in terms of 2-theta degrees, at about 9.6, 11.5, 16.4, 19.2, and 23.8±0.2 degrees;
    c) a Differential Scanning calorimetry (DSC) thermogram substantially the same as shown in FIG. 4;
    d) a Differential Scanning calorimetry (DSC) thermogram with three endothermic events having an onset at about 189.2° C. and a peak at about 191.9° C.
    e) a Thermogravimetric Analysis (TGA) pattern substantially the same as shown in FIG. 4;
    f) a Thermogravimetric Analysis (TGA) pattern with a about 1.0% w/w loss from about 23.8° C. to about 150° C.; or
    g) combinations thereof.

13. A crystalline form of (S)-5-benzyl-N-(5-methyl-4-oxo-2,3,4,5-tetrahydropyrido [3,2-b][1,4]oxazepin-3-yl)-4H-1,2,4-triazole-3-carboxamide, characterized as Form C.

14. The crystalline form of claim 13, having an X-ray powder diffraction pattern derived using Cu(Kα) radiation comprising three, four, five, six or more peaks, in terms of 2-theta_degrees, selected from the group consisting of: 9.8, 10.2, 14.8, 15.2, 18.1, 20.4, and 22.3±0.2 degrees.

15. The crystalline form of claim 13, having the X-ray powder diffraction pattern substantially in accordance with that shown in FIG. 5.

16. The crystalline form of claim 13, characterized by a differential scanning calorimetry (DSC) curve comprising an endotherm at about 124.9° C. and an endothermic peak at 131.3° C.

17. The crystalline form of claim 13, characterized as having one or more of:
    a) an X-ray powder diffraction (XRPD) pattern substantially the same as shown in FIG. 5;
    b) an X-ray powder diffraction (XRPD) pattern derived using Cu(Kα) radiation with peaks, in terms of 2-theta degrees, at about 9.8, 10.2, 14.8, 15.2, and 20.4±0.2 degrees;
    c) a Differential Scanning calorimetry (DSC) thermogram substantially the same as shown in FIG. 7;
    d) a Differential Scanning calorimetry (DSC) thermogram with three endothermic events having an onset at about 124.9° C. and a peak at about 131.3° C.
    e) a Thermogravimetric Analysis (TGA) pattern substantially the same as shown in FIG. 7;
    f) a Thermogravimetric Analysis (TGA) pattern with a about 5.7% w/w loss from about 22.4° C. to about 100° C.; or
    g) combinations thereof.

18. A method of treating a disease or disorder mediated by RIPK1 in a patient in need thereof, comprising administering to the patient an effective amount of the crystalline form of claim 1, wherein the disease or disorder is chosen from inflammatory bowel disease, Crohn's disease, ulcerative colitis, psoriasis, retinal detachment, retinitis pigmentosa, macular degeneration, pancreatitis, atopic dermatitis, rheumatoid arthritis, spondyloarthritis, gout, SoJIA, systemic lupus erythematosus, cutaneous lupus erythematosus, Sjogren's syndrome, systemic scleroderma, anti-phospholipid syndrome, vasculitis, osteoarthritis, non-alcohol steatohepatitis, alcohol steatohepatitis, autoimmune hepatitis, autoimmune hepatobiliary diseases, primary sclerosing cholangitis, nephritis, Celiac disease, autoimmune ITP, transplant rejection, ischemia reperfusion injury of solid organs, sepsis, systemic inflammatory response syndrome, cytokine release syndrome, covid-19 infection, cerebrovascular accident, myocardial infarction, Huntington's disease, Parkinson's disease, allergic diseases, asthma, multiple sclerosis, type I diabetes, Wegener's granulomatosis, pulmonary sarcoidosis, Behcet's disease, interleukin-1 converting enzyme associated fever syndrome, chronic obstructive pulmonary disease, tumor necrosis factor receptor-associated periodic syndrome, peridontitis, trauma, ischemia, stroke, cardiac infarction, infection, lysosomal storage disease, Gaucher's disease, Krabbe disease, Niemann-Pick disease, sepsis, amyotrophic lateral sclerosis (ALS/Lou Gehrig's Disease), HIV-associated dementia, retinal degenerative disease, glaucoma, age related macular degeneration, psoriatic arthritis, Friedreich's ataxia, Lewy body disease, spinal muscular atrophy, brain injury, spinal cord injury, dementia, diabetic neuropathy, polyglutamine (polyQ) diseases, Fahr disease, Menke's disease, Wilson's disease, cerebral ischemia, and a prion disorder.

* * * * *